(12) United States Patent
Yau et al.

(10) Patent No.: US 11,603,356 B2
(45) Date of Patent: Mar. 14, 2023

(54) AMORPHOUS FORM OF A COMPLEMENT COMPONENT C5A RECEPTOR

(71) Applicant: CHEMOCENTRYX, INC., Mountain View, CA (US)

(72) Inventors: Kwok Yau, Sunnyvale, CA (US); Kenken Luong, San Jose, CA (US); Rajinder Singh, Belmont, CA (US); Yibin Zeng, Foster City, CA (US); Penglie Zhang, Foster City, CA (US); Manmohan Reddy Leleti, Dublin, CA (US); Rebecca M. Lui, Mountain View, CA (US)

(73) Assignee: CHEMOCENTRYX, INC., San Carlos, CA (US)

( * ) Notice: Subject to any disclaimer, the term of this patent is extended or adjusted under 35 U.S.C. 154(b) by 204 days.

(21) Appl. No.: 17/091,001

(22) Filed: Nov. 6, 2020

(65) Prior Publication Data

US 2021/0139426 A1    May 13, 2021

Related U.S. Application Data

(60) Provisional application No. 62/932,644, filed on Nov. 8, 2019.

(51) Int. Cl.
*C07D 211/60* (2006.01)
*A61K 9/00* (2006.01)

(52) U.S. Cl.
CPC .......... *C07D 211/60* (2013.01); *A61K 9/0019* (2013.01)

(58) Field of Classification Search
CPC ............................ C07D 211/60; A61K 9/0019
USPC ........................................................ 514/330
See application file for complete search history.

(56) References Cited

U.S. PATENT DOCUMENTS

| | | | |
|---|---|---|---|
| 7,923,564 B2 | 4/2011 | Thygesen et al. |
| 8,445,515 B2 | 5/2013 | Fan et al. |
| 8,906,938 B2 | 12/2014 | Fan et al. |
| 9,126,939 B2 | 9/2015 | Fan et al. |
| 9,573,897 B2 | 2/2017 | Fan et al. |
| 10,035,768 B2 | 7/2018 | Fan et al. |
| 10,660,897 B2 | 5/2020 | Fan et al. |
| 11,026,935 B2 | 5/2021 | Singh et al. |
| 11,149,009 B2 | 10/2021 | Li et al. |
| 11,427,541 B2 | 8/2022 | Singh et al. |
| 2010/0311753 A1 | 12/2010 | Fan et al. |
| 2011/0275639 A1 | 11/2011 | Fan et al. |
| 2015/0141425 A1 | 5/2015 | Fan et al. |
| 2017/0065604 A1 | 3/2017 | Fan et al. |
| 2017/0114017 A1 | 4/2017 | Fan et al. |
| 2018/0072668 A1* | 3/2018 | Fan .......................... A61P 29/00 |
| 2019/0062275 A1 | 2/2019 | Fan et al. |
| 2019/0134020 A1 | 5/2019 | Deng et al. |
| 2021/0139427 A1 | 5/2021 | Singh et al. |
| 2022/0096453 A1 | 3/2022 | Singh et al. |

FOREIGN PATENT DOCUMENTS

| | | |
|---|---|---|
| WO | 2010/075257 A1 | 1/2010 |
| WO | 2016/053890 A1 | 4/2016 |
| WO | 2019/236820 A1 | 12/2019 |

OTHER PUBLICATIONS

U.S. Appl. No. 17/091,019, filed Nov. 6, 2020, Singh et al.
U.S. Appl. No. 17/091,044, filed Nov. 6, 2020, Singh et al.
International Search Report and Written Opinion dated Feb. 3, 2021 corresponding to PCT/US2020/059280 filed Nov. 6, 2020; 9 pages.
International Search Report and Written Opinion dated Feb. 8, 2021 corresponding to PCT/US2020/059287 filed Nov. 6, 2020; 9 pages.
International Search Report and Written Opinion dated Mar. 18, 2021 corresponding to PCT/US2020/059291 filed Nov. 6, 2020; 14 pages.
Anonymously Disclosed IP.com Prior Art Database Technical Disclosure [IP.com No. IPCOM000255250D with an IP.com Electronic Publication Date of Sep. 12, 2018] submitted in a Third Party Observed filed Jul. 27, 2021 corresponding to PCT/US2020/059287 with additional comments; 6 pages.
Pubchem, SID 237279170, Available Date: Feb. 13, 2015 [retrieved on Jan. 5, 2021]; Retrived form the Internet <URL: https://pubchem.ncbi.nlm.nih.gov/substance /237279170>; 8 pages.
International Preliminary Report on Patentability (Chapter II) dated Apr. 25, 2022 corresponding to PCT/US2020/059280 filed Nov. 6, 2020; 6 pages.

\* cited by examiner

*Primary Examiner* — Kristin A Vajda
(74) *Attorney, Agent, or Firm* — Mintz Levin Cohn Ferris Glovsky and Popeo PC

(57) ABSTRACT

Provided herein is an amorphous form of a complement component 5a receptor having the formula of Compound 1

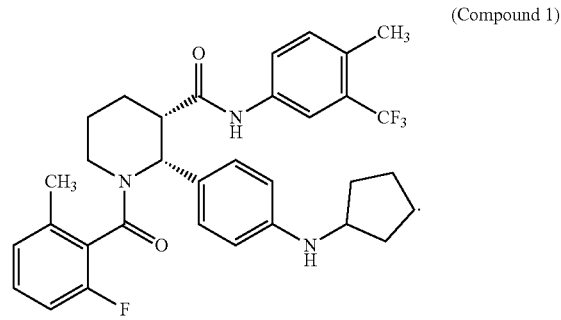

(Compound 1)

Also provided herein are pharmaceutical compositions and methods of treatment using the amorphous form of Compound 1, described herein.

43 Claims, 16 Drawing Sheets

AMORPHOUS FORM OF A COMPLEMENT COMPONENT C5A RECEPTOR

CROSS-REFERENCES TO RELATED APPLICATIONS

This application claims the benefit of priority under 35 U.S.C § 119(e) to U.S. Provisional Application Ser. No. 62/932,644 filed Nov. 8, 2019, the disclosure of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The complement system plays a central role in the clearance of immune complexes and in immune responses to infectious agents, foreign antigens, virus infected cells and tumor cells. Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The complement system is composed of a group of proteins that are normally present in the serum in an inactive state. Activation of the complement system encompasses mainly three distinct pathways, i.e., the classical, the alternative, and the lectin pathway (V. M. Holers, *In Clinical Immunology: Principles and Practice*, ed. R. R. Rich, Mosby Press; 1996, 363-391): 1) The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. 2) The alternative pathway is a magnesium-dependent cascade which is activated by deposition and activation of C3 on certain susceptible surfaces (e.g. cell wall polysaccharides of yeast and bacteria, and certain biopolymer materials). 3) The lectin pathway involves the initial binding of mannose-binding lectin and the subsequent activation of C2 and C4, which are common to the classical pathway (Matsushita, M. et al., *J. Exp. Med.* 176: 1497-1502 (1992); Suankratay, C. et al., *J. Immunol.* 160: 3006-3013 (1998)).

The activation of the complement pathway generates biologically active fragments of complement proteins, e.g. C3a, C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al., *J. Immunol.* 99: 1211-1216 (1967)). It is composed of two polypeptide chains, α and β, with approximate molecular weights of 115 kD and 75 kD, respectively (Tack, B. F. et al., *Biochemistry* 18: 1490-1497 (1979)). Biosynthesized as a single-chain promolecule, C5 is enzymatically cleaved into a two-chain structure during processing and secretion. After cleavage, the two chains are held together by at least one disulfide bond as well as noncovalent interactions (Ooi, Y. M. et al., *J. Immunol.* 124: 2494-2498(1980)).

Recent work has identified (2R,3S)-2-(4-(cyclopentylamino)phenyl)-1-(2-fluoro-6-methylbenzoyl)-N-(4-methyl-3-(trifluoromethyl)phenyl)piperidine-3-carboxamide, Compound 1

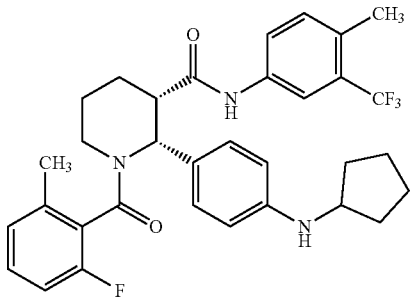 [SMILES: Cc1ccc(NC(=O)[C@H]2CCCN(C(=O)c3c(C)cccc3F)[C@H]2c2ccc(NC3CCCC3)cc2)cc1C(F)(F)F]

as useful for treating C5a mediated diseases. Despite this identification, the efficient delivery of biologically relevant amounts of Compound 1 remains challenging. For example, the poor solubility of Compound 1 in the aqueous environment makes preparing bioavailable formulations particularly difficult.

As such, there is a need to identify solid forms of Compound 1 that can improve important biological characteristics such as solubility, dissolution rate, and bioavailability, without sacrificing stability and potency. The present disclosure addresses these needs and provides related advantages as well.

BRIEF SUMMARY OF THE INVENTION

Provided herein is an amorphous form of Compound 1, methods of making the same, and pharmaceutical compositions prepared using an amorphous form of Compound 1.

In some aspects, provided herein is an amorphous form of (2R,3S)-2-(4-(cyclopentylamino)phenyl)-1-(2-fluoro-6-methylbenzoyl)-N-(4-methyl-3-(trifluoromethyl)phenyl)piperidine-3-carboxamide, Compound 1

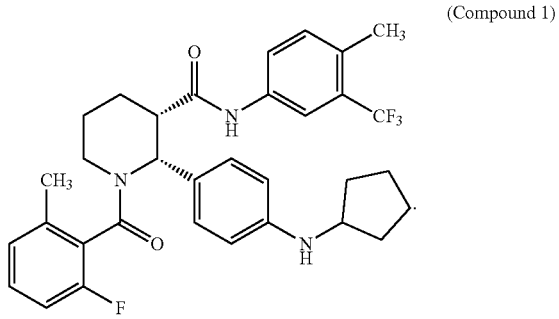 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

The amorphous form of Compound 1 can be characterized using various techniques including, but not limited to, X-ray powder diffraction (XRPD), differential scanning calorimetry (DSC), thermal gravimetric analysis (TGA), dynamic vapor sorption (DVS), and microscopy. Relevant characterizing features from the listed techniques are further described herein.

In additional aspects, provided herein are methods of making an amorphous form of Compound 1. In some embodiments, a methods of preparing an amorphous form of Compound 1 comprises
  a) dissolving Compound 1 in a polar, aprotic solvent to form a solution; and
  b) spray drying the solution to form an amorphous form of Compound 1.

In additional aspect, provided herein are methods for preparing an amorphous form of Compound 1, the method comprising
  a) dissolving Compound 1 in a polar, aprotic solvent to form a solution, wherein the concentration of Compound 1 in the solution is no more than 0.3 g/mL;
  b) optionally filtering the solution to form a filtrate; and
  c) removing solvent from the solution or the filtrate to form an amorphous form of Compound 1.

DETAILED DESCRIPTION OF THE INVENTION

I. General

The present disclosure provides an amorphous form of Compound 1. This form advantageously increases aqueous solubility of the compound, providing an opportunity to prepare, for example, pharmaceutical compositions that can deliver biologically relevant amounts of Compound 1 without the need for administering excessive volumes of liquid. Surprisingly, the amorphous form of Compound 1 disclosed herein exhibits low hygroscopicity and is physically stable under high humidity conditions. Comparatively, most amorphous materials, lacking a long-range, ordered lattice, are highly hygroscopic and unstable under high humidity conditions.

II. Definitions

The terms "about" and "around," as used herein to modify a numerical value, indicate a close range around that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

"Compound 1" is a chemical compound having an IUPAC name of (2R,3 S)-2-(4-(cyclopentylamino)phenyl)-1-(2-fluoro-6-methylbenzoyl)-N-(4-methyl-3-(trifluoromethyl) phenyl)piperidine-3-carboxamide, and the structure shown below:

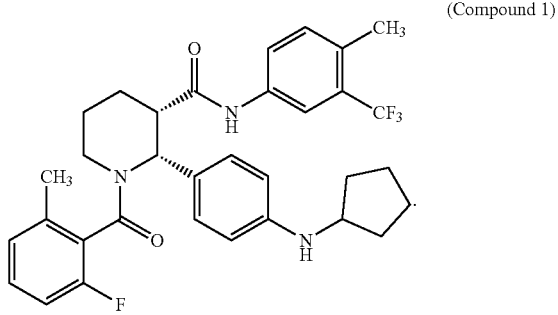 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

"Amorphous form" refers to a solid form of a compound having no definite crystal structure, i.e., lacking a regularly ordered, repeating pattern of constituent molecules.

"Substantially free" refers to an amount of 10% or less of another form, preferably 8%, 5%, 4%, 3%, 2%, 1%, 0.5%, or less of another form.

The term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

As used herein, a condition is considered "responsive to C5a receptor modulation" if modulation of C5a receptor activity results in the reduction of inappropriate activity of a C5a receptor.

The term "individual" refers to mammals, which includes primates (especially humans), domesticated companion animals (such as dogs, cats, horses, and the like) and livestock (such as cattle, pigs, sheep, and the like), with dosages as described herein. In some embodiments, the term "individual" refers to a human.

III. Detailed Description of Embodiments

A. Amorphous Form of Compound 1

In some aspects, provided herein is an amorphous form of Compound 1

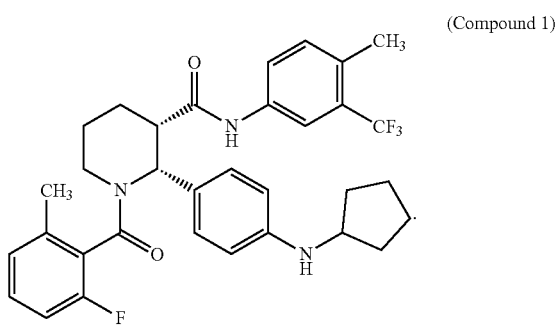 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

Figure 2:
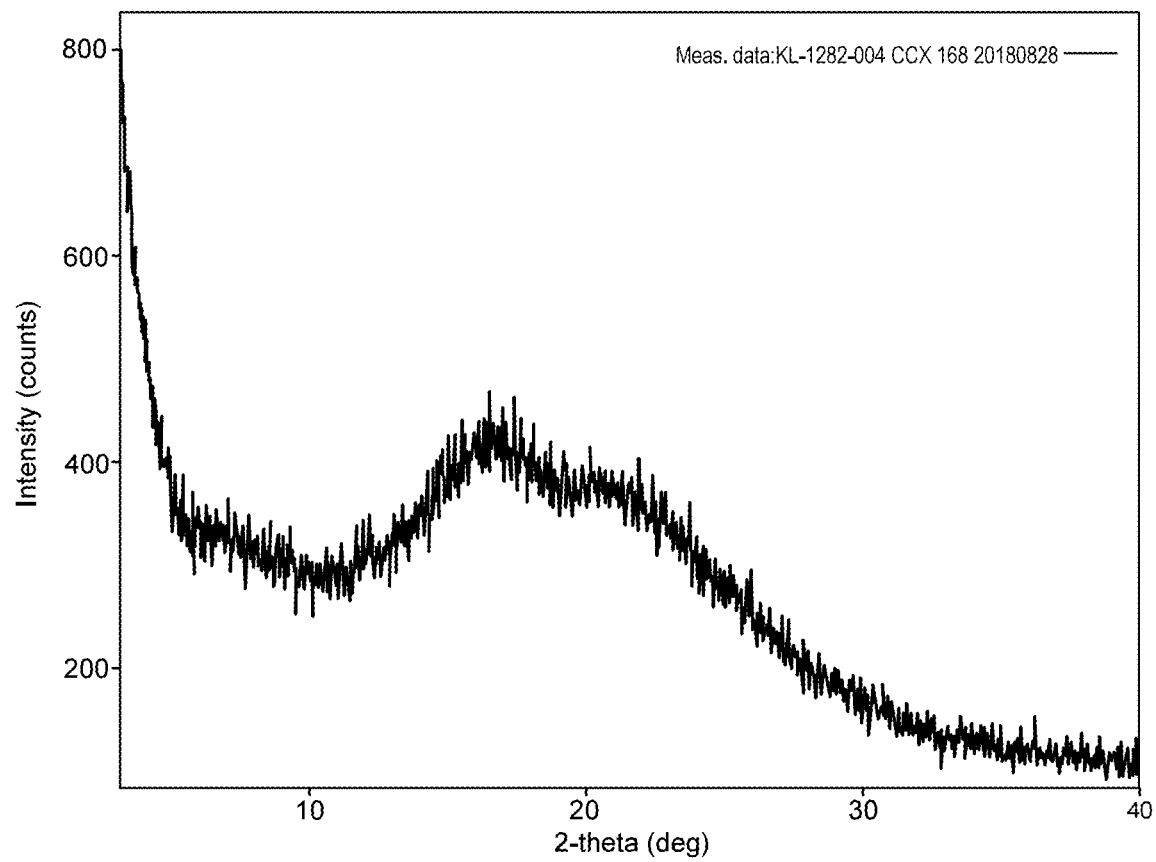
FIG. 2 shows an X-ray powder diffraction (XRPD) pattern of the amorphous form of Compound 1 described in Example 2, Method 1.

In some embodiments, the amorphous form of Compound 1 is characterized by an X-ray powder diffraction pattern having no distinct peaks, which is substantially free of other forms of Compound 1. In some embodiments, the amorphous form of Compound 1 is characterized by an X-ray powder diffraction pattern substantially in accordance with FIG. 2.

Differential scanning calorimetry (DSC) can also be used to characterize the amorphous form of Compound 1 described herein. In some embodiments, the amorphous form of Compound 1 is characterized by a glass transition temperature of about 108° C., as determined by differential scanning calorimetry. In some embodiments, the amorphous form of Compound 1 is characterized by a differential scanning calorimetry (DSC) thermogram substantially in accordance with FIG. 4.

Thermal gravimetric analysis (TGA) is another technique that can be used to characterize the amorphous form of Compound 1 described herein. In some embodiments, the amorphous form of Compound 1 is characterized by a weight loss of about 0.015% up heating to around 235° C., as measured by thermal gravimetric analysis (TGA). In some embodiments, the amorphous form of Compound 1 is characterized by a thermal gravimetric analysis (TGA) thermogram substantially in accordance with FIG. 5.

Figure 6:
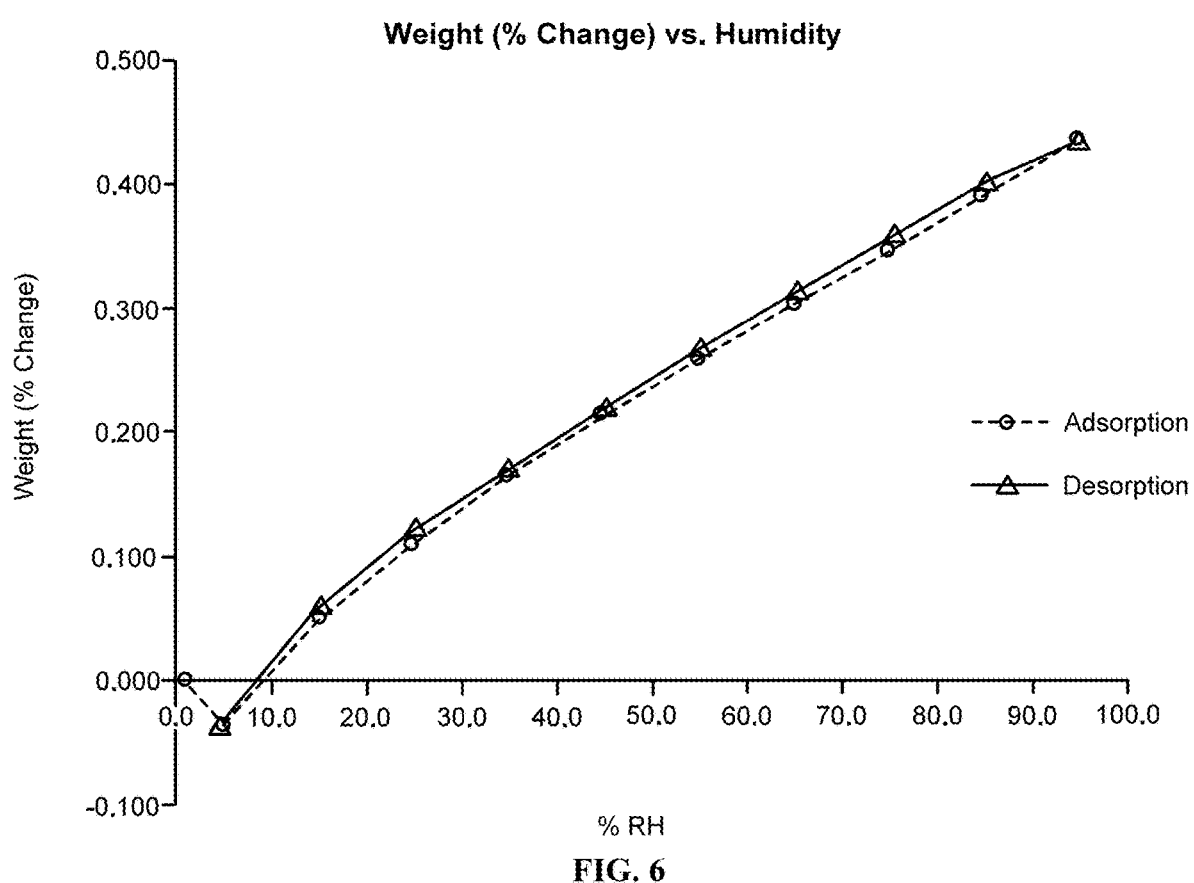
FIG. 6 shows dynamic vapor sorption (DVS) plot of the amorphous form of Compound 1. Adsorption data points are open circles; Desorption data points are open triangles.

Dynamic vapor sorption (DVS) is an additional method that can be used to characterize the amorphous form of Compound 1 described herein. In some embodiments, the amorphous form of Compound 1 is characterized by a weight gain of about 0.44% after undergoing a dynamic vapor sorption (DVS) cycle from about 0% relative humidity (RH) to about 95% RH at 25° C. In some embodiments, the amorphous form of Compound 1 is characterized by a weight gain of about 0.31% after undergoing a dynamic vapor sorption (DVS) cycle from about 0% relative humidity (RH) to about 65% RH at 25° C. In some embodiments, the amorphous form of Compound 1 is characterized by a dynamic vapor sorption (DVS) plot that does not exhibit any hysteresis between adsorption and desorption. In some embodiments, the amorphous form of Compound 1 is characterized by a dynamic vapor sorption (DVS) plot substantially in accordance with FIG. 6.

Microscopy can also be used to characterize the amorphous form of Compound 1 described herein. In some embodiments, scanning electron microscopy (SEM) is used. In some embodiments, the amorphous form of Compound 1 is characterized by an SEM image having predominantly spherical particles. In some embodiments, the spherical particles are about 2 μm to 50 μm, as determined by SEM. In some embodiments, the amorphous form of Compound 1 is characterized by scanning electron microscopy (SEM) images substantially in accordance with FIG. 8A, FIG. 8B, FIG. 8C, or FIG. 8D.

Figure 9A:
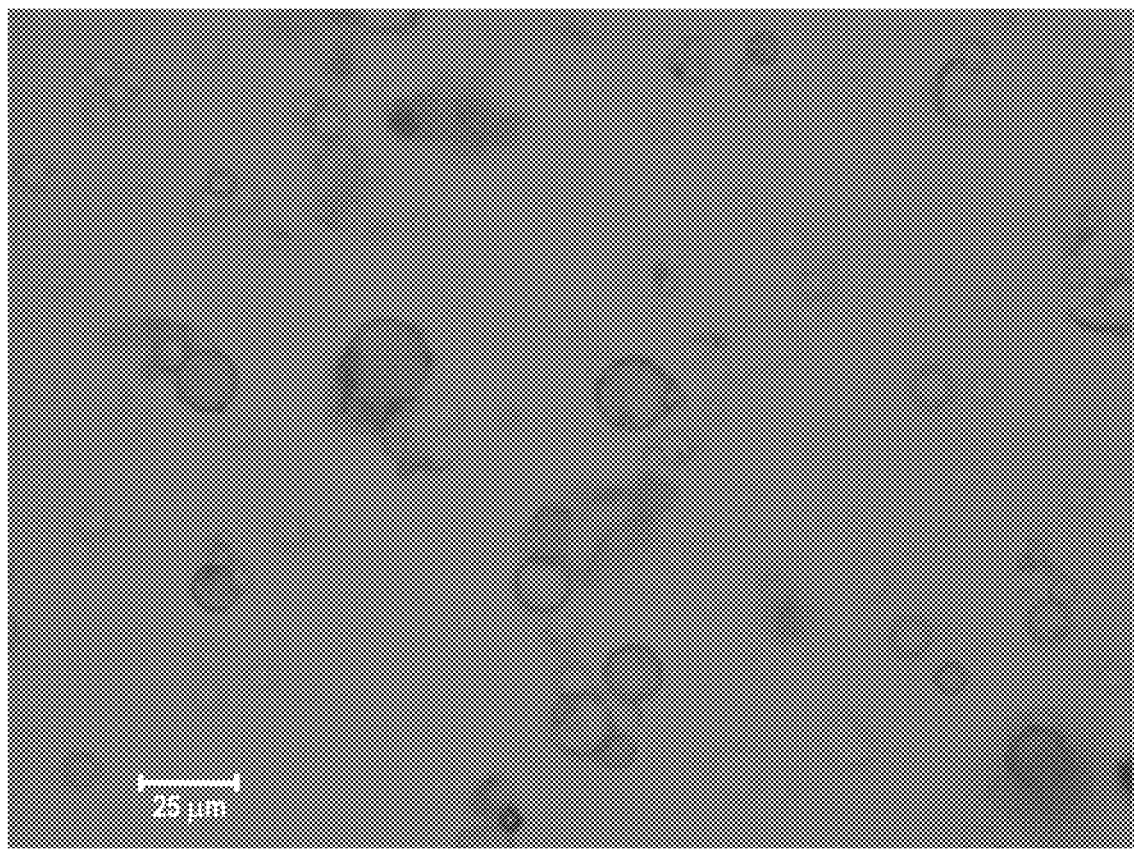
FIGS. 9A-9C show polarized light microscopy (PLM) images of the amorphous form of Compound 1. The magnification shown is 40×. Panels A, B, and C are images from different sample preparations.
Figure 9B:
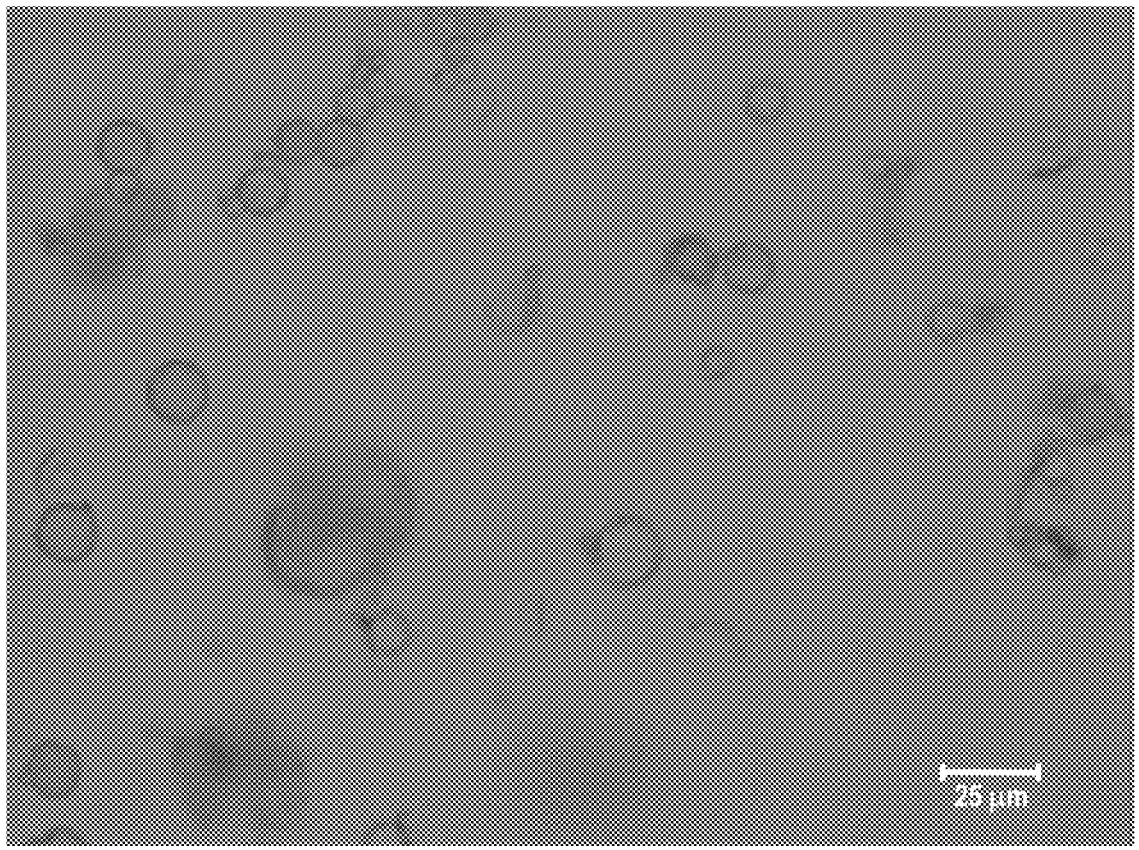
Figure 9C:
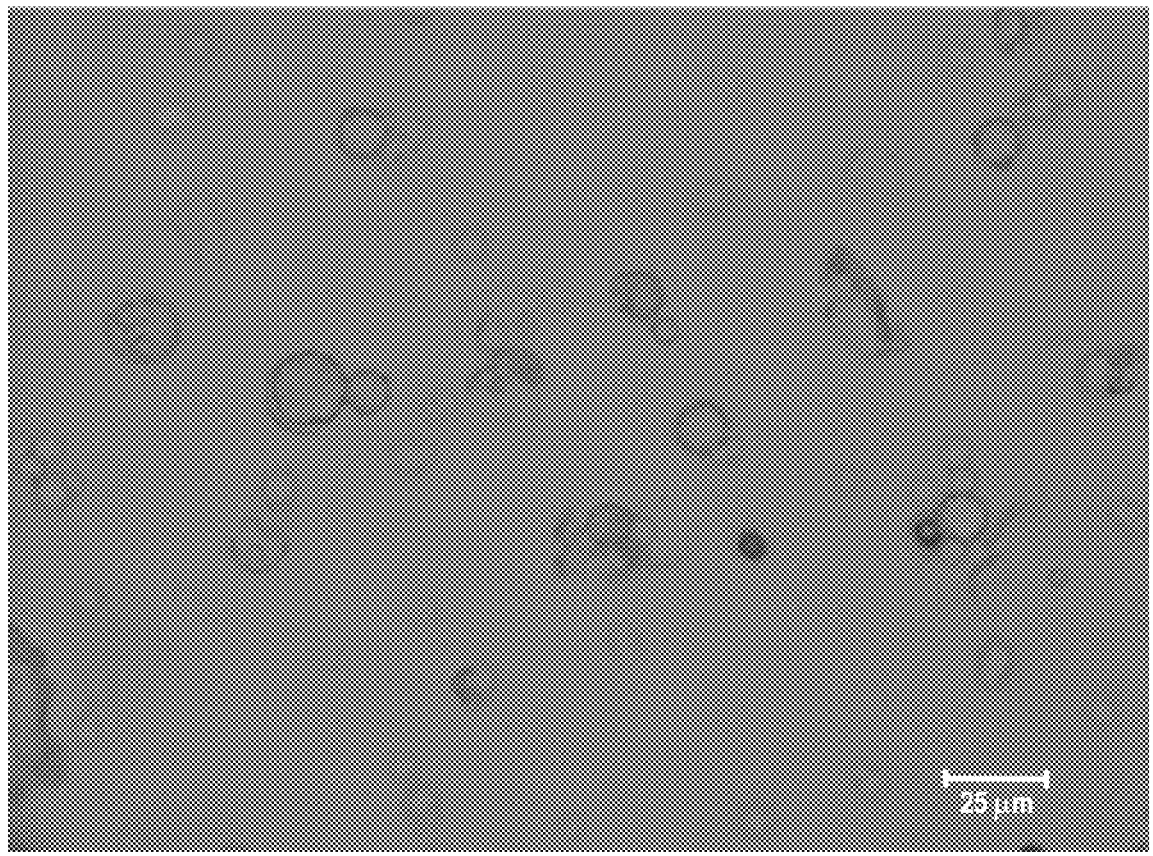

Polarized light microscopy (PLM) is another technique that can be used to characterize the amorphous form of Compound 1 described herein. In some embodiments, the amorphous form of Compound 1 is characterized by a polarized light microscope (PLM) profile lacking birefringence. In some embodiments, the amorphous form of Compound 1 is characterized by polarized light microscope (PLM) profile substantially as shown in FIG. 9A, FIG. 9B, or FIG. 9C.

B. Methods of Making an Amorphous Form of Compound 1

In some aspects, provided herein are methods for preparing an amorphous form of Compound 1, the method comprising a) dissolving Compound 1 in a polar, aprotic solvent to form a solution; and b) spray drying the solution to form an amorphous form of Compound 1.

In some embodiments suitable polar, aprotic solvents include, but are not limited to, dimethyl sulfoxide (DMSO), toluene, dimethylacetamide (DMAc), dioxane, isopropyl acetate (IPAc), tetrahydrofuran (THF), acetone, and dichloromethane (DCM), acetonitrile (MeCN), and the like, as well as mixtures thereof. In some embodiments the polar, aprotic solvent is tetrahydrofuran (THF), acetone, dichloromethane (DCM) or mixtures thereof. In some embodiments the polar, aprotic solvent is tetrahydrofuran (THF). In some embodiments the polar, aprotic solvent is acetone. In some embodiments the polar, aprotic solvent is dichloromethane (DCM) or mixtures thereof.

In some embodiments, the solution is formed at room temperature. In some embodiments, forming the solution includes heating the solution. One of skill in the art will appreciate that the heating temperature will depend, in part, on one or more factors including the particular solvent and the quantity of the solvent. Such factors will also determine, to an extent, the length of time required to dissolve Compound 1. The solution can be heated to, for example, 40° C., 50° C., 60° C., 70° C. or more.

Any suitable length of the time for forming the solution can be used, ranging from a few minutes to several hours. For example, the mixture containing Compound 1 and the one or more polar, aprotic solvents can be mixed, with or without heating, for about 10 minutes, or about 20 minutes, or 30 minutes, or about 40 minutes, or about 1 hour or longer.

A person of skill in the art will readily recognize that there are a number of commercially available apparatuses for spray drying a sample, each of these are embraced by the current application, including a Buchi B290 Spray Dryer.

In some embodiments, the spray dryer is heated to a temperature of from about 50° C. to about 150° C. In some embodiments, the spray dryer is heated to a temperature of from about 70° C. to about 90° C. In some embodiments, the spray dryer is heated to a temperature of about 80° C.

In some embodiments, the spray dryer forces the solution through the nozzle by a pressurized gas. Various pressures can be used to achieve the desired solid form. In some embodiments, the pressurized gas comprises molecular nitrogen.

In some embodiments, a certain amount of Compound 1 is dissolved in the polar, aprotic solvent. In some embodiments, the concentration of Compound 1 dissolved in polar, aprotic solvent is from about 0.05 g/mL to 2 g/mL. In some embodiments, the concentration of Compound 1 dissolved in polar, aprotic solvent is from about 0.1 g/mL to 1.5 g/mL. In some embodiments the concentration of Compound 1 dissolved in polar, aprotic solvent is from about 0.2 g/mL to 1 g/mL. In some embodiments, the concentration of Compound 1 dissolved in polar, aprotic solvent is from about 0.2 g/mL to 0.5 g/mL. In some embodiments, the concentration of Compound 1 dissolved in polar, aprotic solvent is from about 0.3 g/mL to 0.5 g/mL. In some embodiments, the concentration of Compound 1 dissolved in polar, aprotic solvent is no more than 0.5 g/mL. In some embodiments, the concentration of Compound 1 dissolved in polar, aprotic solvent is about 0.25 mg/mL. In some embodiments, the concentration of Compound 1 dissolved in polar, aprotic solvent is about 0.375 mg/mL.

In additional aspects, provided herein are methods for preparing an amorphous form of Compound 1, the process comprising
  d) dissolving Compound 1 in a polar, aprotic solvent to form a solution,
    wherein the concentration of Compound 1 in the solution is no more than 0.3 g/mL;
  e) optionally filtering the solution to form a filtrate; and
  f) removing solvent from the solution or the filtrate to form an amorphous form of Compound 1.

Suitable polar aprotic solvents include the solvents discussed in the method above. In some embodiments the polar, aprotic solvent is tetrahydrofuran (THF), acetone, dichloromethane (DCM) or mixtures thereof. In some embodiments the polar, aprotic solvent is tetrahydrofuran (THF). In some embodiments the polar, aprotic solvent is acetone. In some embodiments the polar, aprotic solvent is dichloromethane (DCM) or mixtures thereof.

Generally, the amount of Compound 1 in the polar, aprotic solvent does not exceed 0.3 g/mL. This concentration of Compound 1 avoids undesired nucleation and crashing out of Compound 1 into a non-amorphous form. In some embodiments, the concentration of Compound 1 is the polar, aprotic solvent does not exceed 0.28, 0.26, 0.24, 0.22, 0.2, 0.18, 0.16, 0.14, or 0.12 g/mL. In some embodiments, the concentration of Compound 1 in the polar, aprotic solvent is about 0.11 g/mL.

The optional filtration step can be performed using a number of commercially available filters, including polyethylene filters. Various sizes of filters can also be used including ~2, 4, 6, 8, 10, 12, 14, 16, 18, 20 μm, or larger pore sizes. In some embodiments the pore size of the filter is 10 The filtration can be done using standard techniques such as gravity, suction, and pressure.

Solvent can be removed from the solution or the filtrate using a variety of techniques. For example, solvent can be removed by lower the pressure or increasing the temperature of the solution or the filtrate. In some embodiments, a rotary evaporator is used for removing the solvent. In some embodiments, oven drying is also used. Suitable temperatures include, about 30°, 35°, 40°, 45°, 50°, 55°, 60°, 65° C. or warmer.

C. Pharmaceutical Compositions

As demonstrated herein, the amorphous form of Compound 1 advantageously provides increased aqueous solubility as well as increased pharmacokinetic exposure. Accordingly, provided herein are pharmaceutical compositions comprising an amorphous form of Compound 1 or liquid pharmaceutical compositions prepared using the amorphous form of Compound 1. Pharmaceutical compositions will include one or more pharmaceutically acceptable excipients.

The pharmaceutical compositions containing the amorphous form of Compound 1 may be in a form suitable for oral use, for example, as tablets, troches, lozenges, liquid formulations, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the amorphous form of Compound 1 in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the amorphous form of Compound 1 is mixed with an inert solid diluent, for example, calcium carbonate, calcium phosphate or kaolin, or as soft gelatin capsules wherein the amorphous form of Compound 1 is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions for oral use contain the amorphous form of Compound 1 in admixture with excipients suitable for the manufacture of aqueous suspensions. Such excipients are suspending agents, for example sodium carboxymethylcellulose, methylcellulose, hydroxy-propylmethylcellulose, hydroxy-propylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate as well as other poloxamers (e.g. Poloxamer F-68). The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Accordingly, provided herein is aqueous suspension comprising the amorphous form of Compound 1 and at least one excipient. In some embodiments, the at least one excipient is at least one suspending agent and/or at least one wetting agent as described above.

Oily suspensions for oral use may be formulated by suspending the amorphous form of Compound 1 in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

The pharmaceutical compositions may be in the form of a sterile injectable or infusable aqueous or oleagenous solution or suspension. This solution or suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, isotonic sodium chloride solution, isotonic aqueous buffer solutions, as well as mixtures of saline, a disintegrating agent such as PEG (e.g. PEG 200, PEG 400, PEG 800, etc), and nonionic surfactants such as Tween80. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables and infusables. Compositions for injectable or infusable administration optionally include a local anesthetic such as lignocaine to ease pain at the site of the injection. Ingredients can be supplied pre-mixed or supplied separately, with mixing of the ingredients occurring shortly before use. In some embodiments, mixing shortly before use is desirable to take advantage of the high initial solubility of the amorphous form of Compound 1 in certain liquid formulation mixtures.

Injectable or infusible compositions includes, but is not limited to, intravenous administration, intramuscular administration as well as subcutaneous or intrasternal injection. Accordingly, in some embodiments, provided herein is an injectable or infusible solution comprising Compound 1 and at least one wetting agent or solvent, wherein the intravenous pharmaceutical composition is prepared using the amorphous form of Compound 1 described herein. In some embodiments, the injectable or infusible solution is prepared for intravenous administration. In some embodiments, the injectable or infusible solution is prepared for intramuscular administration. In some embodiments, the injectable or infusible solution is prepared for subcutaneous injection. In some embodiments, the injectable or infusible solution is prepared for intrasternal injection. In some embodiments, the at least one wetting agent or solvent in the injectable or infusible pharmaceutical composition includes saline, a disintegrating agent, and nonionic surfactant.

Injectable or infusible compositions can be prepared at any time that is convenient for the medical practitioner or user; this includes shortly before use or well in advance of use. In some embodiments, the composition is prepared shortly before use. Shortly before use includes 0-24 hours before use, 0-10 hours before use, 0-5 hours before use, or 0-1 hours before use. In some embodiments, the injectable or infusible composition is prepared 0-5 hours before use. Well in advance typically refers to one or more days before use. Accordingly, also provided herein are methods of preparing injectable or infusible solution. The method including, dissolving the amorphous form of Compound 1 with the at least one wetting agent or solvent to prepare an injectable or infusible solution; and administering the injectable or infusible solution to a subject in need thereof.

Dispersible powders and granules suitable for preparation of an aqueous oral formulations or oral suspensions by the addition of water provide the amorphous form of Compound 1 in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The compounds of the present invention may also be administered in the form of suppositories for rectal administration of the drug. These compositions can be prepared by mixing the amorphous form of Compound 1 with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

D. Methods of Treatment

Also provided herein are methods of treating individuals suffering from conditions that are responsive to C5a receptor modulation.

In some aspects provided herein are methods of treating an individual suffering from or susceptible to a disease or disorder involving pathologic activation of C5a receptors, comprising administering to the individual an effective amount of an amorphous form of Compound 1 or a pharmaceutical formulation including Compound 1 as described herein.

In some embodiments, the amorphous form of Compound 1 described herein is used for treating patients suffering from conditions that are responsive to C5a receptor modulation. Conditions that can be Treated by C5a Modulation:

Autoimmune disorders—e.g., Rheumatoid arthritis, systemic lupus erythematosus, Guillain-Barre syndrome, pancreatitis, C3 glomerulopathy (C3G), hidradenitis suppurativa (HS), lupus nephritis, lupus glomerulonephritis, immunoglobulin A (IgA) nephropathy, psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, hyperacute rejection of transplanted organs; and the like.

Inflammatory disorders and related conditions—e.g., Neutropenia, sepsis, septic shock, Alzheimer's disease, multiple sclerosis, stroke, inflammatory bowel disease (IBD), age-related macular degeneration (AMD, both wet and dry forms), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. The amorphous form of Compound 1 described herein may also be useful in the treatment of age-related macular degeneration (Hageman et al, *P.N.A.S.* 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of an amorphous form of Compound 1 described herein may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Diseases of Vasculitis—Vasculitic diseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The amorphous form of Compound 1 described herein can be used to treat vasculitis, including anti-neutrophil cytoplasmic antibody associate vasculitis (or ANCA-associated vasculitis, which includes microscopic polyangiitis, eosinophilic granulomatosis with polyangitis, and granulomatosis with polyangiitis, which is also known as Wegener's disease), Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV infection and AIDS—the amorphous form of Compound 1 described herein may be used to inhibit HIV infection, delay AIDS progression or decrease the severity of symptoms or HIV infection and AIDS.

Neurodegenerative disorders and related diseases— Within further embodiments, the amorphous form of Compound 1 described herein may be used to treat Alzheimer's disease, multiple sclerosis, and cognitive function decline associated with cardiopulmonary bypass surgery and related procedures.

Cancers—The amorphous form of Compound 1 described herein are also useful for the treatment of cancers and precancerous conditions in a subject. Specific cancers that can be treated include, but are not limited to, sarcomas, carcinomas, and mixed tumors. Exemplary conditions that may be treated according to the present invention include fibrosarcomas, liposarcomas, chondrosarcomas, osteogenic sarcomas, angiosarcomas, lymphangiosarcomas, synoviomas, mesotheliomas, meningiomas, leukemias, lymphomas, leiomyosarcomas, rhabdomyosarcomas, squamous cell carcinomas, basal cell carcinomas, adenocarcinomas, papillary carcinomas, cystadenocarcinomas, bronchogenic carcinomas, melanomas, renal cell carcinomas, hepatocellular carcinomas, transitional cell carcinomas, choriocarcinomas, seminomas, embryonal carcinomas, wilm's tumors, pleomorphic adenomas, liver cell papillomas, renal tubular adenomas, cystadenomas, papillomas, adenomas, leiomyomas, rhabdomyomas, hemangiomas, lymphangiomas, osteomas, chondromas, lipomas and fibromas.

In some embodiments, the amorphous form of Compound 1 described herein can be used for the treatment of diseases selected from the group consisting of sepsis (and associated disorders), COPD, rheumatoid arthritis, lupus nephritis and multiple sclerosis.

In some embodiments, the amorphous form of Compound 1 described herein can be used for the treatment of diseases selected from the group consisting of anti-neutrophil cytoplasmic antibody associate (ANCA) vasculitis, C3 glomerulopathy, hidradenitis suppurativa, and lupus nephritis.

Treatment methods provided herein include, in general, administration to a patient an effective amount of an amorphous form of Compound 1. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of the amorphous form of Compound 1 described herein. The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the amorphous form of Compound 1 described herein is administered to a patient (e.g., a human) orally. In some embodiments, the amorphous form of Compound 1 described herein is administered to a patient (e.g., a human) intravenously, intramuscularly, or via subcutaneous or intrasternal injection. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro.

For treatment of most disorders via oral administration, a person of skill in the art may determine the appropriate frequency of administration. In some embodiments, a frequency of administration of 4 times daily or less is preferred. In some embodiments, a dosage regimen of 2 times daily is used. In some embodiments, once daily administration is used. The patient may be administered an amorphous form of Compound 1 in a fed or fasted state. In some embodiments, the patient takes the amorphous form Compound 1 with food. In some embodiments, the patient takes the amorphous form of Compound 1 without food.

For treatment of most disorders via intravenous, intramuscular administration or via subcutaneous or intrasternal injection, a person of skill in the art may determine the appropriate frequency of administration. In some embodiments, the frequency of administration is about once every two weeks. In some embodiments, the frequency of administration is about once every week. In some embodiments, the frequency of administration is about three times a week. In some embodiments, the frequency of administration is about 2 to 5 times a week. In some embodiments, the frequency of administration is about once every other day. In some embodiments, the frequency of administration is about once a day.

It will be understood, however, that the specific dose level and treatment regimen for any particular patient will depend upon a variety of factors including the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of the amorphous form of Compound 1 that may be combined with the carrier materials to produce a single dosage form will vary depending upon the host treated and the particular mode of administration. Dosage unit forms will generally contain between from about 1 mg to about 500 mg of the amorphous form of Compound 1. When administered orally, transdermally, intravaneously, or subcutaneously, it is preferred that sufficient amount of the amorphous form of Compound 1 be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient amounts of the amorphous form of Compound 1 should be administered to achieve a local concentration of approximately 1 micromolar.

E. Combination Therapy

The presently disclosed methods may include combination therapy with one or more additional therapeutic agents that are used in the treatment, prevention, suppression or amelioration of the diseases or conditions involving pathologic activation of C5a receptors. Such one or more additional therapeutic agents may be administered, by a route and in an amount commonly used therefor, contemporaneously or sequentially with the amorphous form of Compound 1. When the amorphous form of Compound 1 is used contemporaneously with the additional therapeutic agent, a pharmaceutical composition containing such other drugs in addition to the amorphous form of Compound 1 is preferred. Accordingly, the pharmaceutical compositions of the present disclosure include those that also contain one or more other active ingredients or therapeutic agents, in addition to the amorphous form of Compound 1.

Examples of the one or more additional therapeutic agents are corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, Mannan-binding lectin serine protease-2 (MASP-2) inhibitors, Factor B inhibitors, Factor D inhibitors, C3aR modulators, C5aR2 modulators, T cell receptor antagonists, PD-1 inhibitors, PD-L1 inhibitors, TIGIT inhibitors, TIM-3 inhibitors, LAG-3 inhibitors, VISTA inhibitors, STING agonists, IDO inhibitors, adenosine receptor modulators, CD39 inhibitors, CD73 inhibitors, antagonists of the chemokine receptors, especially CXCR1, CXCR2, CXCR3, CXCR4, CXCR7, CCR1, CCR2, CCR3, CCR4, CCR5, CCR7, CCR7, CCR9, CX3CR1 and CXCR6, and combinations thereof.

In some embodiments, the additional therapeutic agent used in the therapeutic methods herein, is selected from the group consisting of obinutuzumab, rituximab, ocrelizumab, tositumomab, obinutuzumab, ibritumomab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, NOX-100, LT-1951, OMS721, ALN-CCS, ACH-4471, AMY-101, Acthar gel, and CD4+CD25+ regulatory T-cells, MEDI7814, P32, P59, pembrolizumab, nivolumab, atezolizumab, avelumab, durvalumab, CCX354, CCX721, CCX9588, CCX140, CCX872, CCX598, CCX6239, CCX587, CCX624, CCX282, CCX025, CCX507, CCX430, CCX765, CCX758, CCX771, CCX662, CCX650, and combinations thereof.

IV. Examples

The following examples are provided to help illustrate the described invention and are not intended to limit the scope of what the inventors regard as their invention.

Example 1: Preparation of Free Base Crystalline Form of Compound 1

Crude Compound 1 was prepared essentially as described in WO 2016/053890.

Figure 1:
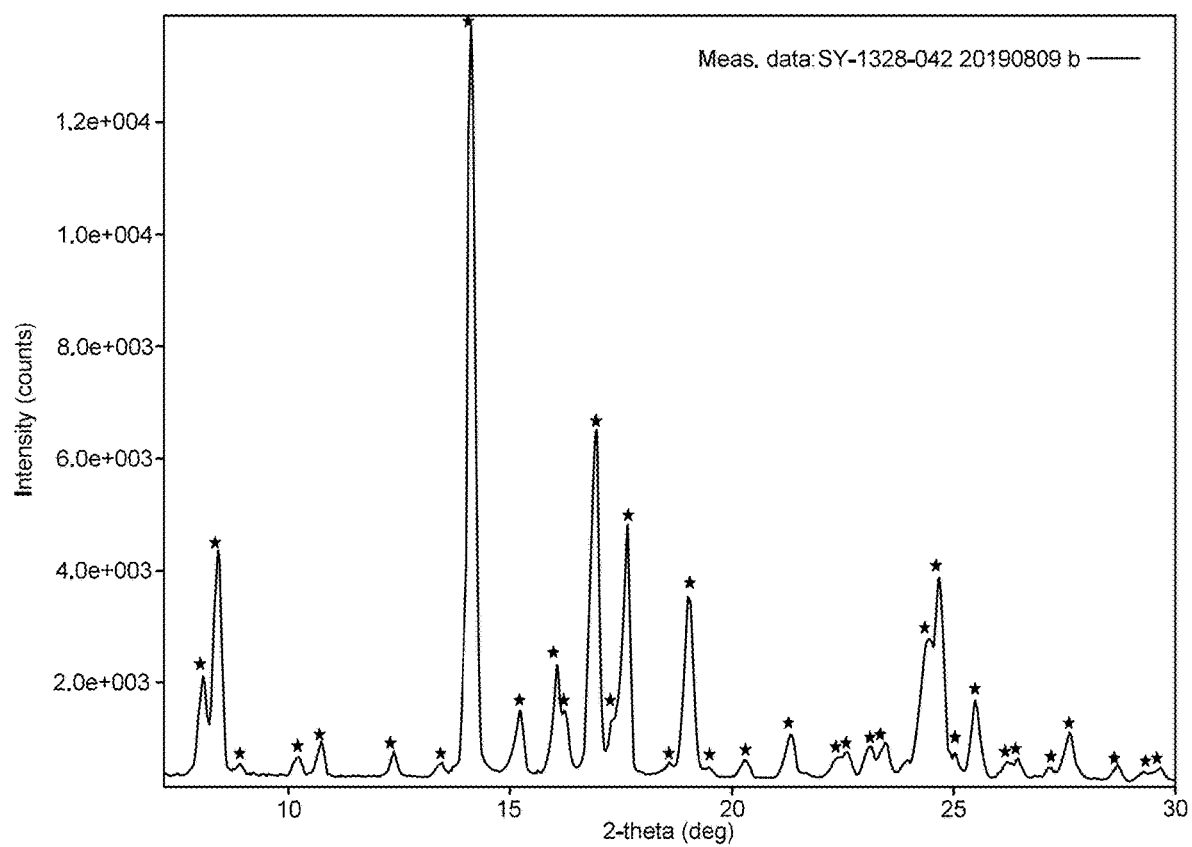
FIG. 1 shows the X-ray powder diffraction (XRPD) pattern of the free base crystalline form described in Example 1.

A free base crystalline form of Compound 1 was prepared by dissolving 18 g of crude Compound 1 in 50 mL acetone with heating at 40° C. (a concentration of about ~0.36 g/mL). The warm solution was passed through a 10 μm polyethylene filter. The solution was then loaded into rotary evaporator at 30° C. bath temperature and 180 rpm rotational speed. The solid collected was dried further in a 45° C. oven for 1 hour. The XRPD data of the crystalline form is shown in FIG. 1, and the table of peaks measured are listed in Table 1, below.

TABLE 1

Significant Peaks of Free Base Crystalline Form of Compound 1
Significant Peaks 2-theta (deg)

| | |
|---|---|
| 8.06 | 20.28 |
| 8.40 | 21.32 |
| 8.88 | 22.36 |
| 10.20 | 22.60 |
| 10.72 | 23.14 |
| 12.35 | 23.46 |
| 13.44 | 24.42 |
| 14.10 | 24.66 |
| 15.21 | 25.05 |
| 16.05 | 25.48 |
| 16.20 | 26.20 |
| 16.92 | 26.44 |
| 17.28 | 27.18 |
| 17.64 | 27.60 |
| 18.58 | 28.70 |
| 19.00 | 29.28 |
| 19.44 | 29.60 |

Example 2: Preparing an Amorphous Form of Compound 1

Method 1

Crude Compound 1 was prepared essentially as described in WO 2016/053890.

Crude Compound 1 (15 grams) was dissolved into 40 mL of acetone at 40° C. temperature. The solution was spray dried using a Buchi B290 Spray Dryer, equipped with a peristaltic pump. The spray drying process was completed by using target inlet temperature of 80° C., target spray rate of 5 mL/min, and process gas flow rate of 20.60 CFM. The spray dried powder collected in the sample collection chamber was the amorphous form of Compound 1 as assessed by XRFD, shown in FIG. 2.

Method 2

Figure 3A:
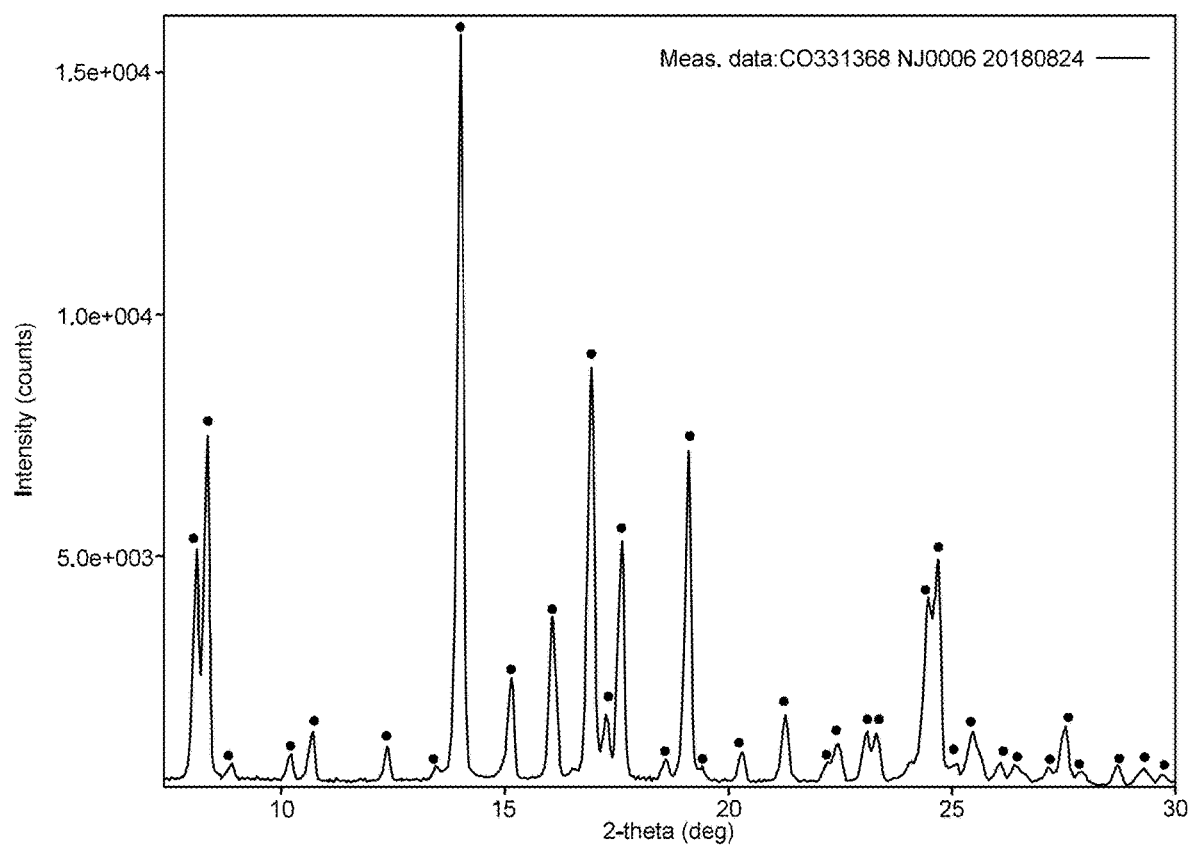
FIGS. 3A-3B show the X-ray powder diffraction (XRPD) pattern of the crystalline starting material (A) and the amorphous product (B) described in Example 2, Method 2.
Figure 3B:
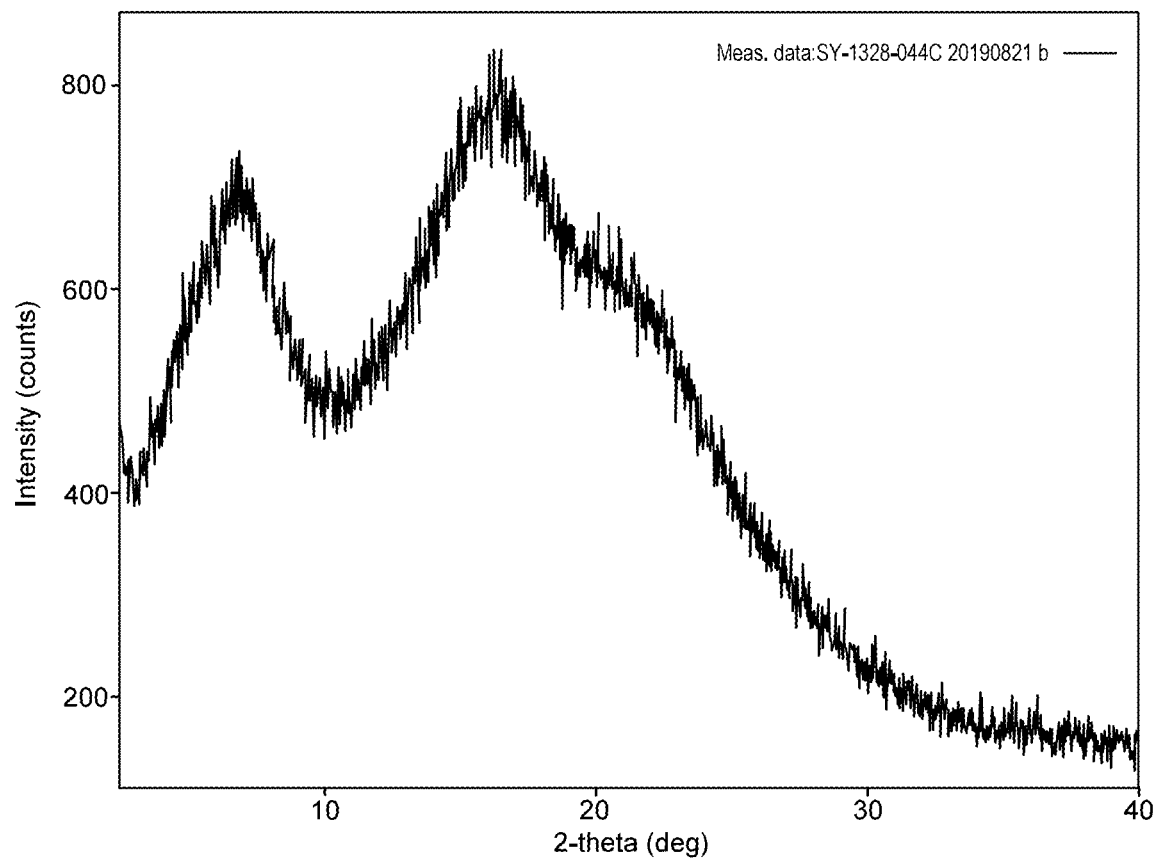
Figure 4:
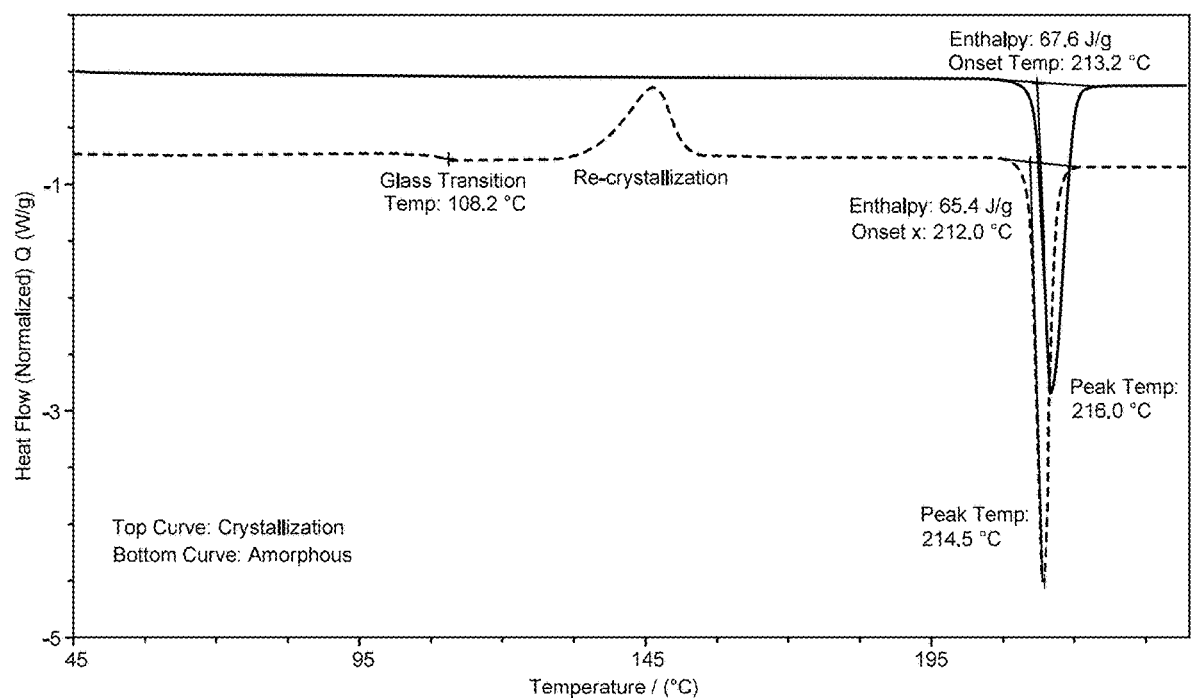
FIG. 4 shows the differential scanning calorimetry (DSC) thermogram of the amorphous form of Compound 1 as well as the crystalline form of Compound 1 (prepared in Example 1).

An amorphous form of Compound 1 was prepared by dissolving 1 g of the free base crystalline form of Compound 1 in 9 mL of acetone without any heating (a concentration of about ~0.11 g/mL). The solution was passed through a 10 μm polyethylene filter by gravity. The solution was then loaded into rotary evaporator at 45° C. bath temperature and 220 rpm rotational speed. The solid collected was dried further in a 45° C. oven for 30 hour. The XRPD data of the starting material (in crystalline form) and the amorphous form produced from Method 2 are shown in FIG. 3A & FIG. 3B. The DSC data of the starting material (in crystalline form) and the amorphous form produced from Method 2 are shown in FIG. 4. Experimental details related to DSC data collection are described in Example 3.

Example 3: Differential Scanning Calorimetry (DSC) and Thermal Gravimetric Analysis (TGA) of the Amorphous Form of Compound 1

To evaluate the physical characteristics of the amorphous form of Compound 1, differential scanning calorimetry data was collected. Differential scanning calorimeter model DSC25 from TA Instruments~Waters LLC was used. Sample was weighed into a standard aluminum pan and sealed by a standard aluminum lid with pinhole. The measurement was completed by using 10° C./min scanning rate, under a nitrogen purge. The DSC analysis determined that the amorphous form exhibits a glass transition temperature at around 108° C. A plot of the DSC thermogram is shown in FIG. 4.

Figure 5:
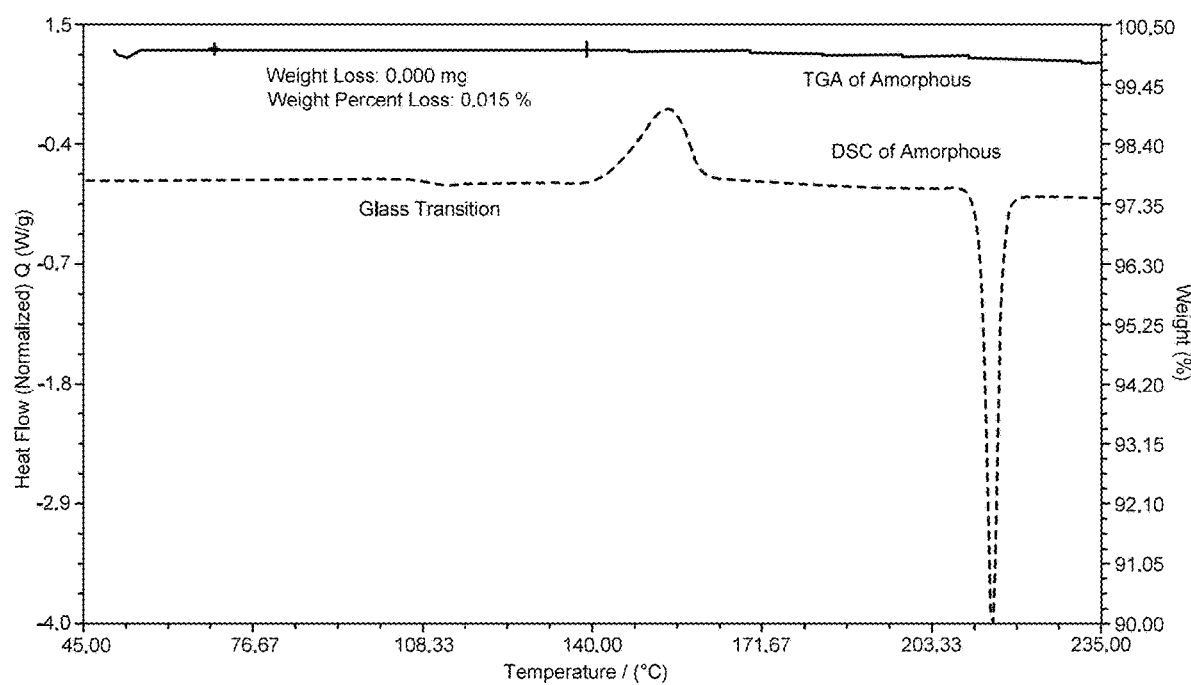
FIG. 5 shows the thermal gravimetric analysis (TGA) thermogram of the amorphous form of Compound 1 as well as the DSC thermogram.

The amorphous form of Compound 1 was also evaluated using thermal gravimetric analysis (TGA). TGA data was collected on a TA instrument Q500 TGA. Each sample was loaded onto a pre-tared platinum crucible; the balance and furnace were purged with nitrogen prior to the analysis with a flow rate set as 40±5 and 60±5 mL/min, respectively. The heating process was programmed to start at the ambient temperature with a 10° C./min ramp. The TGA analysis determined that the amorphous form of Compound 1 exhibits about a 0.015% weight loss upon heating to around 139° C. A plot of the TGA thermogram is shown in FIG. 5.

Example 4: Dynamic Vapor Sorption (DVS) of the Amorphous Form of Compound 1

To evaluate the hygroscopicity and physical stability of the amorphous form of Compound 1 under different humidity, dynamic vapor sorption (DVS) data was collected at 25° C. after the sample was pre-equilibrated at 0% RH to remove unbounded water. DVS was measured using a VTI SGA-100 Vapor Sorption Analyzer. Sorption and desorption data was collected over a range from 5% to 95% RH at 10% RH increments under a nitrogen purge. The equilibrium criterion used for analysis was less than 0.0100% weight change in 5 minutes with a maximum equilibrium time of 3 hours. Parameters for DVS test are listed in Table 2.

TABLE 2

Parameters for DVS test

| Parameters | Value |
|---|---|
| Temperature | 25° C. |
| dm/dt | 0.0100% |
| Min. dm/dt stability duration | 5 min |
| Max. equilibrium time | 3 hours |
| RH range | 5% RH-95% RH-5% RH |
| Humidity increment | 10% RH |
| RH step size | 19 |

Figure 7:
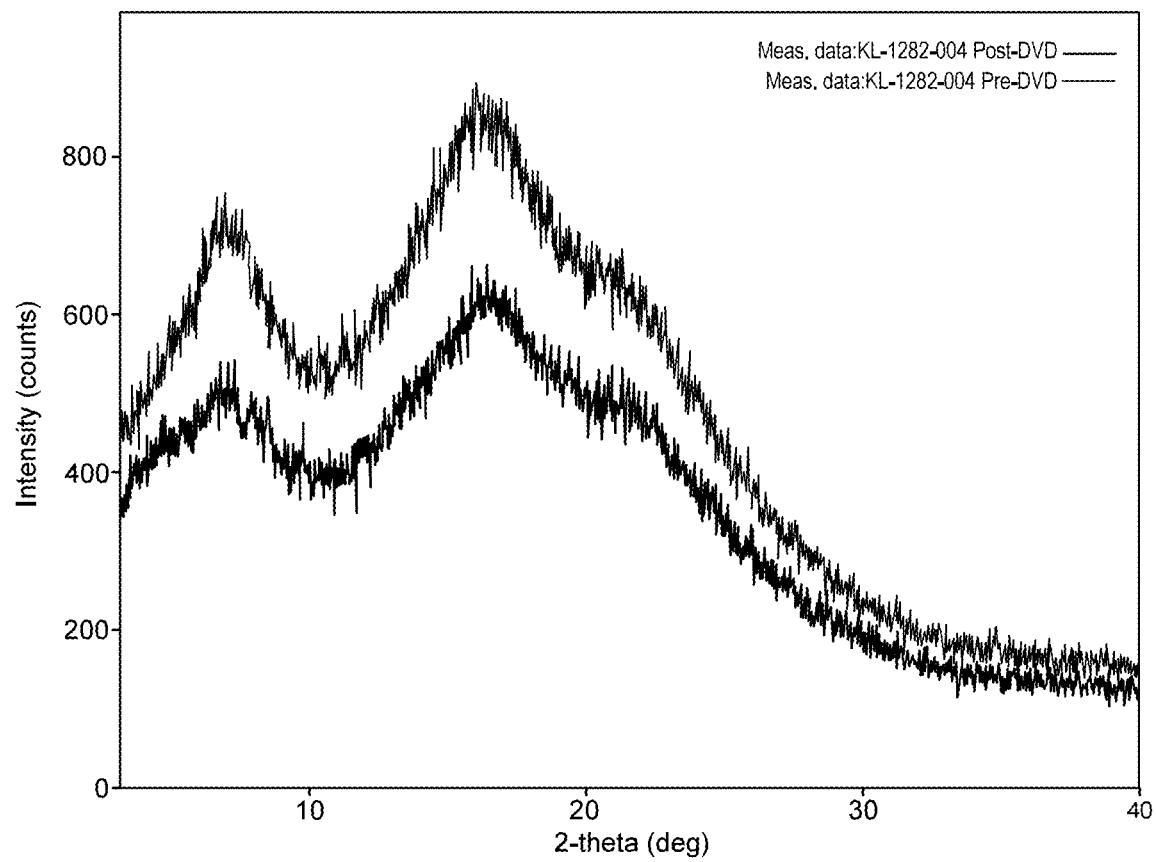
FIG. 7 shows XRPD patterns of the amorphous form of Compound 1 before (upper) and after (lower) DVS.
Figure 8A:
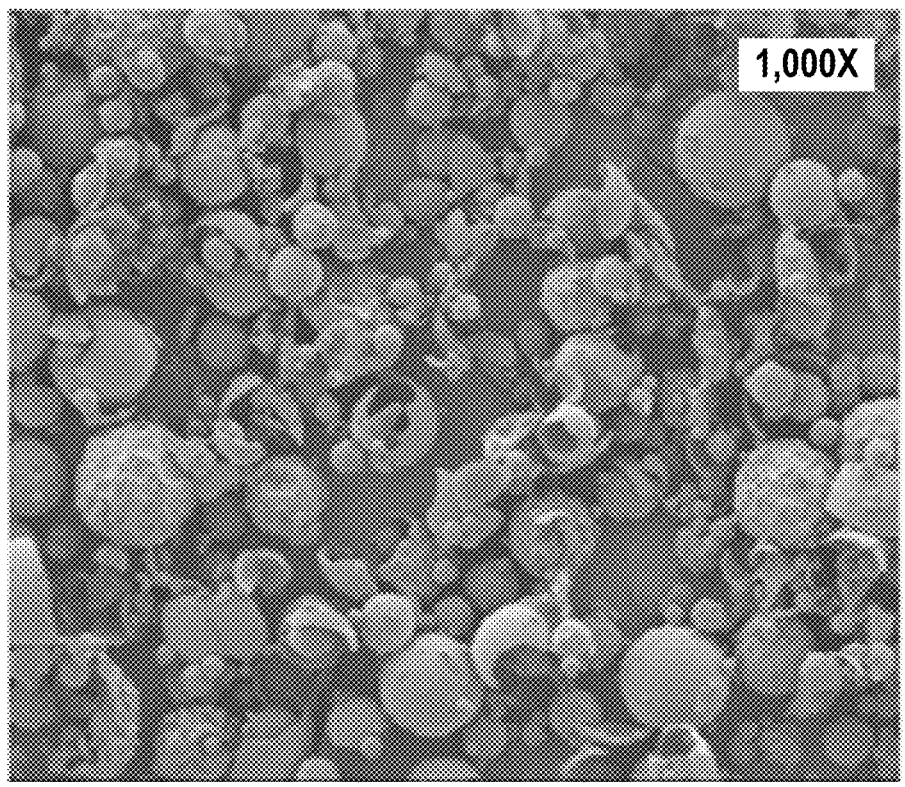
FIGS. 8A-8D show scanning electron microscopy (SEM) images of the amorphous form of Compound 1. The magnifications shown include 1,000× (A), 2,500× (B), 5,000× (C), and 10,000× (D).
Figure 8B:
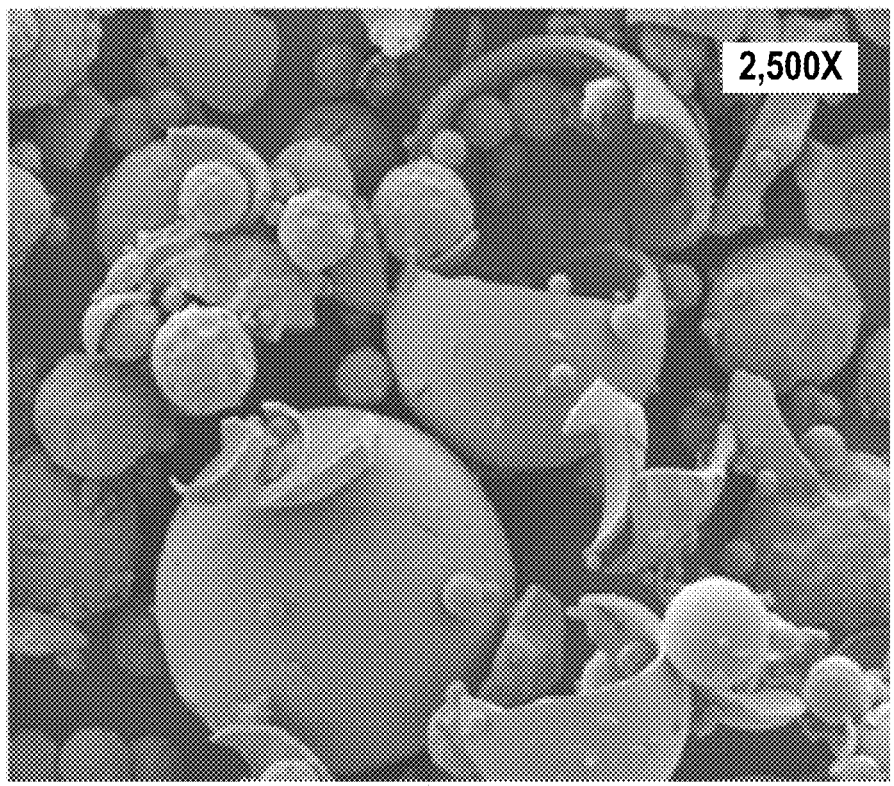
Figure 8C:
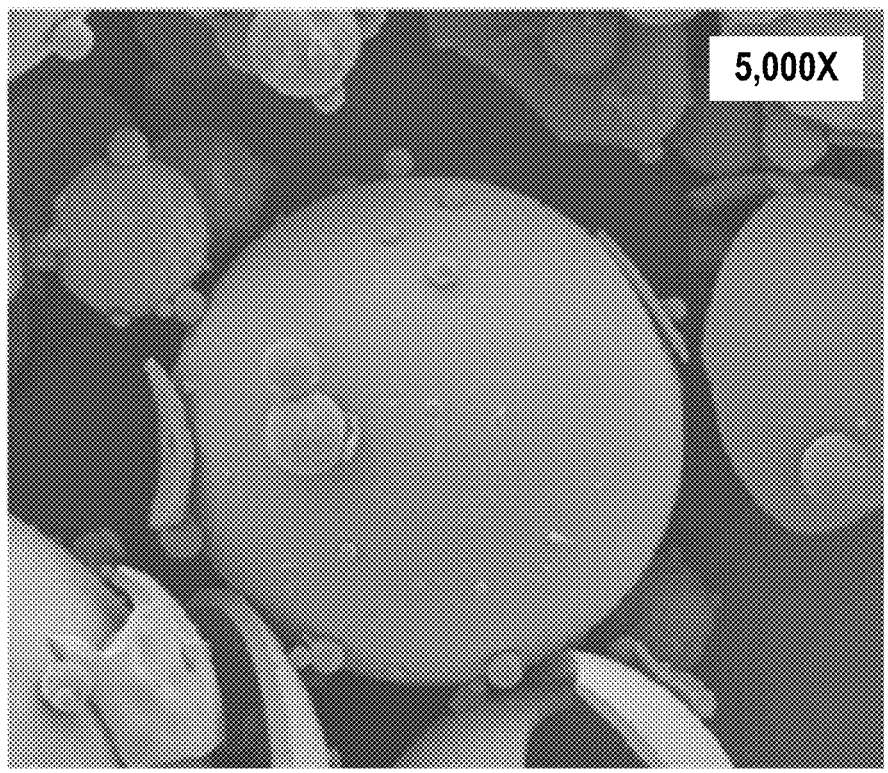
Figure 8D:
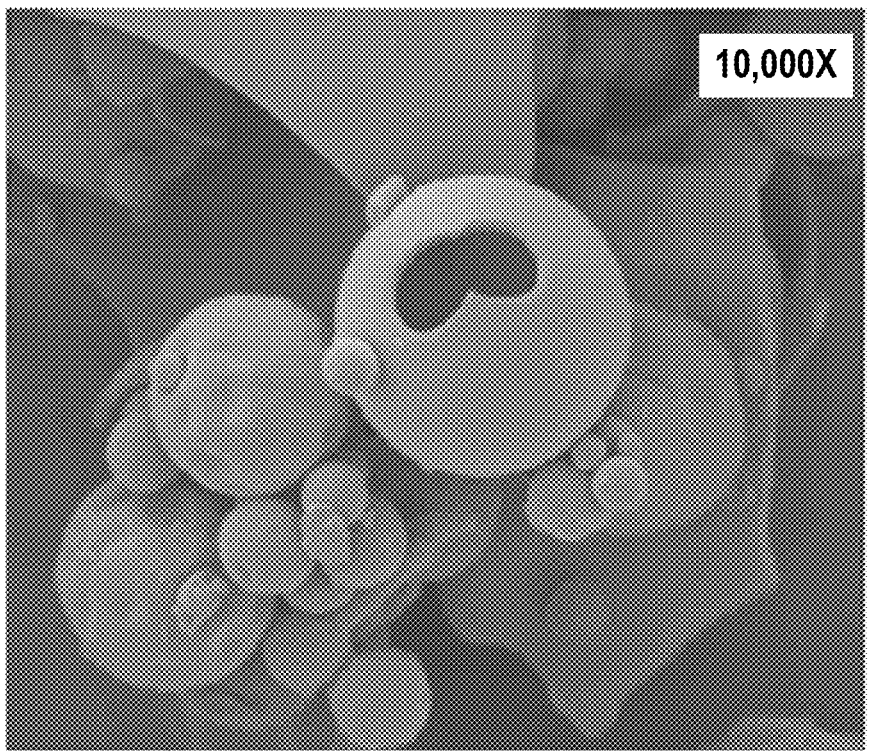

DVS of the amorphous form of Compound 1 showed a weight gain of 0.4% after undergoing a dynamic vapor sorption cycle from about 0% relative humidity (RH) to about 95% RH at 25° C. (FIG. 6), indicating that the amorphous form of Compound 1 has low hygroscopicity. The DVS plot also displayed no hysteresis between adsorption and desorption. Additionally, XRPD results (FIG. 7) showed no form change before and after DVS test.

Example 5: Scanning Electron Microscopy (SEM) Images of the Amorphous Form of Compound 1

A scanning electron microscopy image was obtained by using a FEI Quanta 200 scanning electron microscope equipped with an Everhart Thornley (ET) detector. The images were collected and analyzed by using xTm (v. 2.01) and XT Docu (v. 3.2) software, respectively. The magnification was verified using a National Institute of Standards and Technology (NIST)-Traceable standard. The samples were prepared for analysis by placing a small amount on a carbon adhesive tab supported on an aluminum mount. The sample was then sputter coated twice (in different orientations) with Au/Pd using a Cressington 108 auto Sputter Coater at approximately 20 mA and 0.13 mbar (Ar) for 75 seconds. Representative images of the amorphous form are shown in FIG. 8A-8D. When observed under magnification the crystals were predominantly spherical ranging in size from ~2 to 50 μm.

Example 6: Polarized Light Microscopy (PLM) Images of the Amorphous Form of Compound 1

Polarized light microscopy was performed by using a Leica DM LP microscope equipped with a Spot Insight color camera. Different objectives were used with crossed polarized and a first order red compensator to view the sample. Sample was placed on a glass slide, a #1.5 cover glass was placed over the sample, and a drop of mineral oil was added. Images were acquired at ambient temperature using Spot Advanced software (v. 4.5.9). Micrometer bar was inserted onto the image as a reference for size. Representative images of the amorphous form are shown in FIG. 9A-9C. Notably, when viewing the amorphous form of Compound 1, no birefringence was observed, supporting the conclusion that the solid forms prepared herein are amorphous. When observed under magnification the crystals ranged in size from ~6 to 20 μm.

Example 7: Stability of the Amorphous Form of Compound 1

Figure 10:
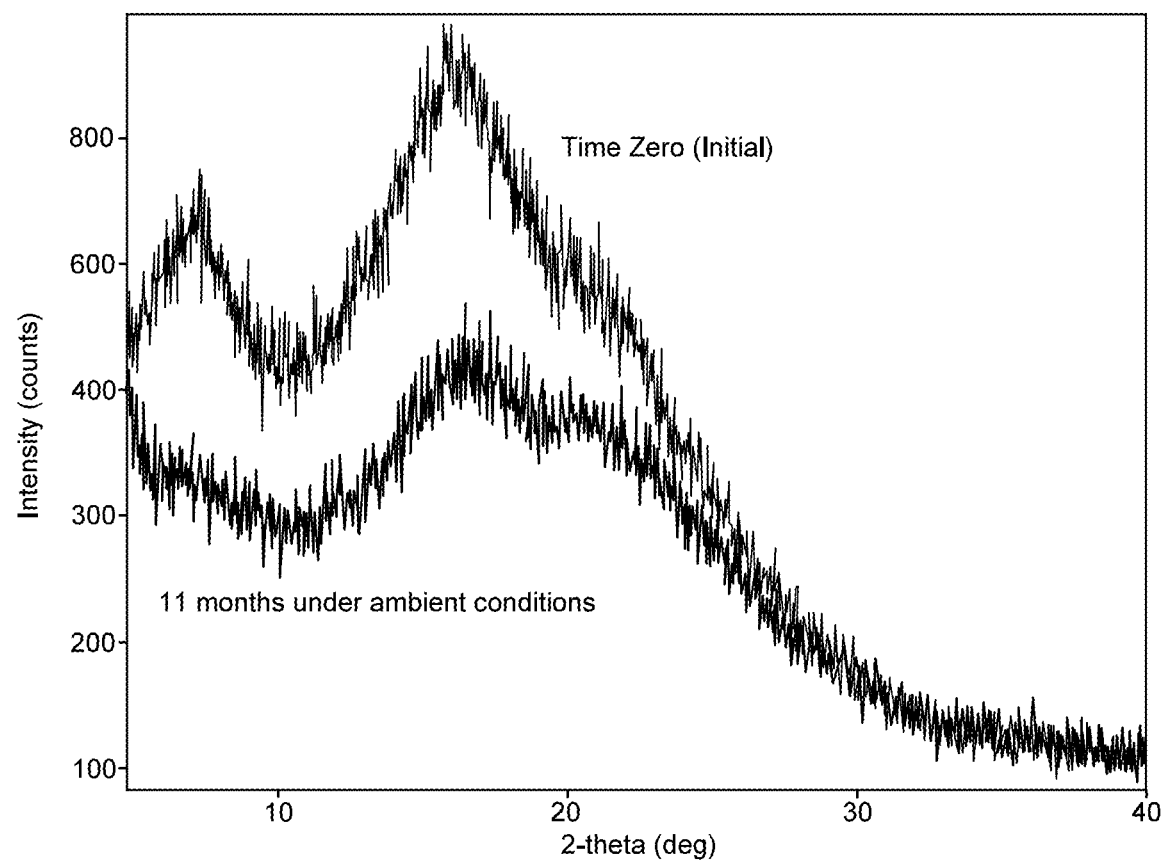
FIG. 10 shows XRPD patterns of the amorphous form of Compound 1 after initial (time zero) preparation (lower) and after 11 months of storage under ambient conditions (upper).

A sample of amorphous form of Compound 1 was tested by XRPD (FIG. 10) when it was freshly prepared (the top XRPD pattern, labeled as "Time Zero (Initial)"). This sample was stored inside a closed glass container under normal ambient laboratory environment. After 11 months, it was tested again by XRPD (the bottom XRPD pattern, labeled as "11 months under ambient condition").

A sample of amorphous form of Compound 1 was tested by different analytical methods and the data was reported in the "Time Zero" column (Table 3). These analytical methods included: HPLC and Karl Fisher (KF). The sample was placed in double Low-Density Polyethylene (LDPE) bags, sealed with a cable tie, then placed in a High-Density Polyethylene (HDPE) bottle with foil and heat-induction sealed, with 0.5 g desiccant between LDPE bags. The HDPE bottle was stored inside an environment chamber at 25° C. and 60% relative humidity (RH). After 12 months inside the environment chamber, the sample was tested again by the same analytical methods. The results are displayed in Table 3.

TABLE 3

Stability Storage Test of the Amorphous Form of Compound 1

| Test | Time Zero | Time 12 months (25° C./60% RH) |
|---|---|---|
| Appearance | Off-white Powder | Off-white Powder |
| Potency (HPLC) | 99.5% w/w | 98.9% w/w |
| Unspecified Individual Related Substances (HPLC) | RRT0.45: <0.05% RRT0.50: <0.05% RRT0.90: 0.05% RRT0.96: <0.05% RRT1.14: 0.05% RRT1.16: <0.05% RRT1.20: 0.22% RRT1.21: 0.06% RRT1.22: <0.05% | RRT0.90: 0.20% RRT0.96: <0.05% RRT1.06: 0.07% RRT1.14: <0.05% |
| Specified Individual Related Substances (HPLC) | RRT1.05: 0.08% | RRT1.05: <0.05% |
| Total Impurities and Related Substances (HPLC) | 0.38% | 0.20% |
| Chiral Purity | 0.0% | 0.0% |
| X-Ray Powder Diffraction | Consistent w/an amorphous form | Consistent w/an amorphous form |
| Water Content (KF) | 0.33% | 0.31% |

Example 8: The Amorphous Form of Compound 1 Provides Improved In Vitro Solubility The in vitro solubility of a crystalline form of Compound 1 and the amorphous form of Compound 1 was tested.

The amorphous form was prepared as described in Example 2, Method 1, and the crystalline form of Compound 1 was prepared as described in Example 1.

Crystalline and amorphous forms of Compound 1 were saturated in three different media: 0.1 N HCl solution, Fasted State Simulated Gastric Fluid (FaSSGF), and Fed State Simulated Intestinal Fluid (FeSSIF). The samples were shaken inside a 37° C. water bath at 40 rpm. The concentration of Compound 1 dissolved in these samples was measured by HPLC at four different time points (0.5, 1, 2 and 4 hours).

TABLE 4

Comparison of Kinetic Solubility between Crystalline Form of Compound 1 and Amorphous Form of Compound 1

| | CCX168 Solubility (μg/mL) at 37° C. | | | | | |
|---|---|---|---|---|---|---|
| | 0.1N HCl (pH 1.06) | | FaSSGF (pH 1.64) | | FeSSIF (pH 4.90) | |
| Time | Crystalline | Amorphous | Crystalline | Amorphous | Crystalline | Amorphous |
| 0.5 Hr. | ND | 47.5 | ND | 9.3 | ND | 6.0 |
| 1 Hr. | ND | 54.0 | ND | 7.8 | ND | 9.9 |

TABLE 4-continued

Comparison of Kinetic Solubility between Crystalline
Form of Compound 1 and Amorphous Form of Compound 1

CCX168 Solubility (μg/mL) at 37° C.

| | 0.1N HCl (pH 1.06) | | FaSSGF (pH 1.64) | | FeSSIF (pH 4.90) | |
|---|---|---|---|---|---|---|
| Time | Crystalline | Amorphous | Crystalline | Amorphous | Crystalline | Amorphous |
| 2 Hr. | ND | 74.7 | ND | BQL | ND | 9.0 |
| 4 Hr. | ND | 61.7 | ND | ND | ND | 7.4 |

ND = Not Detected
BQL = Less than 3.1 μg/mL
FaSSGF = Fasted State Simulated Gastric Fluid
FeSSIF = Fed State Simulated Intestinal Fluid

Example 9: IV Formulations Using the Amorphous Form of Compound 1 Provides Increased Solubility Intravenous (IV) formulations of a crystalline form of Compound 1 and the amorphous form of Compound 1 were prepared by contacting the amorphous of crystalline Compound 1 with saline/PEG400/Tween80 (88:10:1). The crystalline form of Compound 1 was prepared as described in Example 1, the amorphous form of Compound was prepared as described in Example 2, Method 1.

Figure 11:
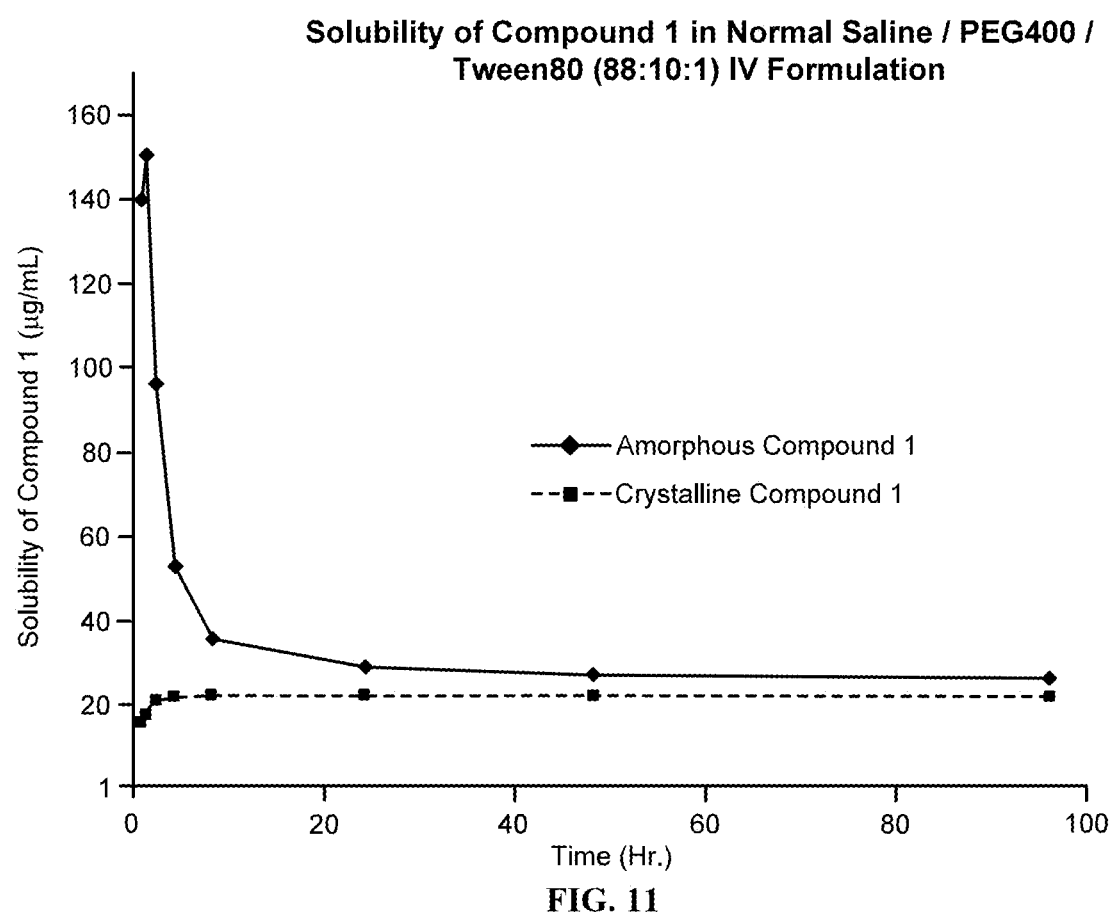
FIG. 11 displays a solubility plot of Compound 1 in an IV formulation when prepared with the amorphous form of Compound 1 (closed circles) and a crystalline form of Compound 1 (closed squares).

As demonstrated in Table 5, below, the amorphous form of Compound 1 improved the aqueous solubility in an IV formulation when compared to the crystalline form, particularly at early time points. A plot of the solubility over time is shown in FIG. 11.

TABLE 5

Solubility in IV Formulation (μg/mL)

| Time (Hr.) | Amorphous Compound 1 | Crystalline Compound 1 |
|---|---|---|
| 0.5 | 140.0 | 15.2 |
| 1 | 150.6 | 17.2 |
| 2 | 96.1 | 20.5 |
| 4 | 52.8 | 21.6 |
| 8 | 35.6 | 22.0 |
| 24 | 28.9 | 21.9 |
| 48 | 26.9 | 21.9 |
| 96 | 26.3 | 21.6 |

Figure 12:
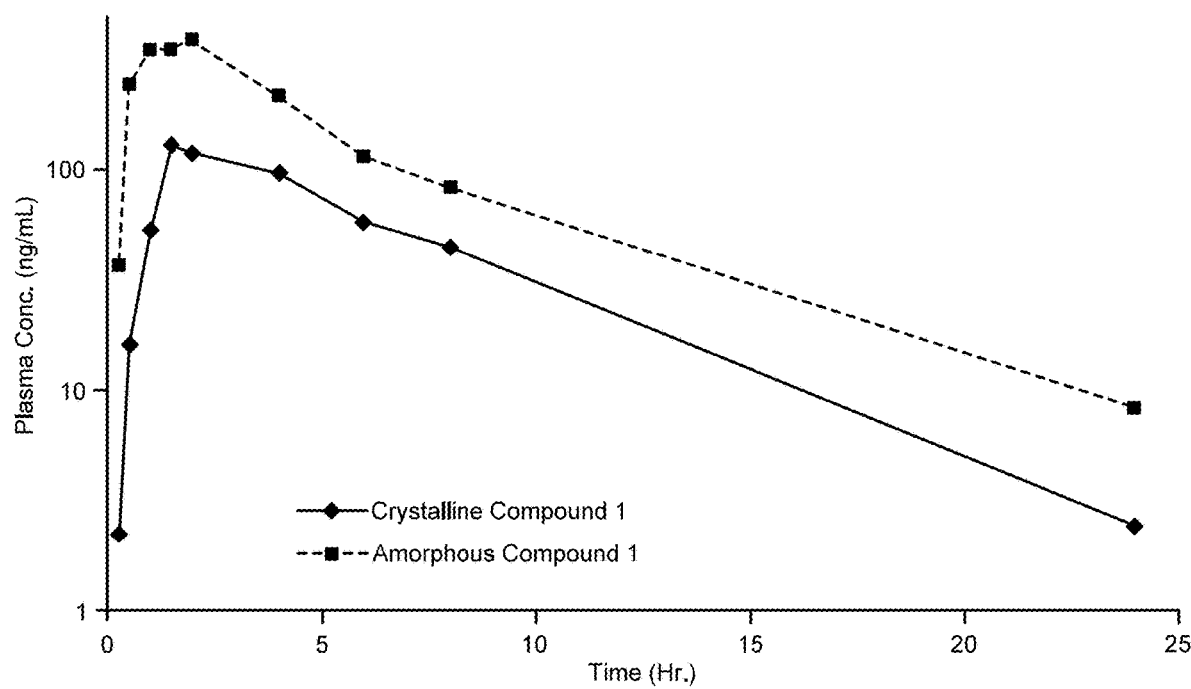
FIG. 12 displays plots of the plasma concentration over time of rats dosed with a liquid suspension formulation containing a crystalline form of Compound 1 (lower) and the same amount of a liquid suspension formulation containing an amorphous form of Compound 1 (upper). Further formulation details are provided in Example 10.

Example 10: Aqueous Suspension Formulations Using the Amorphous Form of Compound 1 Provides Increased Bioavailability An in vivo rat PK study was conducted to compare the PK profile and bioavailability of crystalline form against amorphous form of Compound 1 in an aqueous liquid suspension formulation, which contained 0.5% w/v Hydroxypropyl Cellulose (Klucel GF grade) and 0.5% w/v Poloxamer F-68 (BASF Kolliphor P188). Each animal was orally administrated 10 mg/kg of Compound 1 at 5 mL/kg dosing volume (a dosing concentration of 2 mg/mL). The suspension formulation containing amorphous form of Compound 1 resulted in a significant increase in Cmax and AUC as compared to the formulation containing crystalline form of Compound 1 (Table 6). The PK profile of these two formulations are shown in FIG. 12.

TABLE 6

Comparison of in vivo Rat PK Exposure of Formulation
Containing Crystalline Form of Compound 1 and Amorphous
Form of Compound 1 in an Aqueous Liquid Formulation
(0.5% w/v Klucel GF and 0.5% w/v Poloxamer F-68)

| API Lot | Crystalline Compound 1 | Amorphous Compound 1 |
|---|---|---|
| $C_{max}$ [ng/mL] | 129 | 388 |
| $AUC_{inf}$ [ng · hr/mL] | 996 | 2473 |
| $AUC_{0-t}$ [ng · hr/mL] | 983 | 2412 |
| MRT [hr] | 6 | 5.6 |
| $t_{1/2}$ [hr] | 3.9 | 4.7 |
| $T_{max}$ [hr] | 1.5 | 2 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. An amorphous form of Compound 1

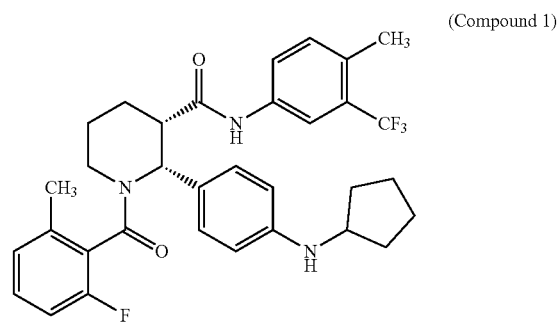 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

characterized by an X-ray powder diffraction pattern having no distinct peaks, which is substantially free of other forms of Compound 1.

2. The amorphous form of Compound 1 according to claim 1, characterized by an X-ray powder diffraction pattern substantially in accordance with FIG. 2.

3. The amorphous form of Compound 1 according to claim 1, further characterized by a glass transition temperature of about 108° C., as determined by differential scanning calorimetry.

4. The amorphous form of Compound 1 according to claim 1, further characterized by a differential scanning calorimetry (DSC) thermogram substantially in accordance with FIG. 4.

5. The amorphous form of Compound 1 according to claim 1, further characterized by a weight loss of about 0.015% up heating to around 235° C., as measured by thermal gravimetric analysis (TGA).

6. The amorphous form of Compound 1 according to claim 1, further characterized a thermal gravimetric analysis (TGA) thermogram substantially in accordance with FIG. 5.

7. The amorphous form of Compound 1 according to claim 1, further characterized by a weight gain of about 0.44% after undergoing a dynamic vapor sorption (DVS) cycle from about 0% relative humidity (RH) to about 95% RH at 25° C.

8. The amorphous form of Compound 1 according to claim 1, further characterized by a weight gain of about 0.31% after undergoing a dynamic vapor sorption (DVS) cycle from about 0% relative humidity (RH) to about 65% RH at 25° C.

9. The amorphous form of Compound 1 according to claim 1, further characterized by a dynamic vapor sorption (DVS) plot that does not exhibit any hysteresis between adsorption and desorption.

10. The amorphous form of Compound 1 according to claim 1, further characterized by a dynamic vapor sorption (DVS) plot substantially in accordance with FIG. 6.

11. The amorphous form of Compound 1 according to claim 1, further characterized by a scanning electron microscopy (SEM) image having predominantly spherical particles.

12. The amorphous form of Compound 1 according to claim 11, wherein spherical particle sizes are about 2 μm to 50 μm, as determined by SEM.

13. The amorphous form of Compound 1 according to claim 1, further characterized by scanning electron microscopy (SEM) image substantially in accordance with FIG. 8A, FIG. 8B, FIG. 8C, or FIG. 8D.

14. The amorphous form of Compound 1 according to claim 1, further characterized by a polarized light microscope (PLM) profile lacking birefringence.

15. The amorphous form of Compound 1 according to claim 1, further characterized by a polarized light microscope (PLM) profile substantially as shown in FIG. 9A, FIG. 9B, or FIG. 9C.

16. A process for preparing an amorphous form of Compound 1 according to claim 1, the process comprising
   a) dissolving Compound 1 in a polar, aprotic solvent to form a solution;
   b) spray drying the solution to form an amorphous form of Compound 1.

17. A process for preparing an amorphous form of Compound 1 according to claim 1, the process comprising
   a) dissolving Compound 1 in a polar, aprotic solvent to form a solution,
      wherein the concentration of Compound 1 in the solution is no more than 0.3 g/mL;
   b) optionally filtering the solution to form a filtrate; and
   c) removing solvent from the solution or the filtrate to form an amorphous form of Compound 1.

18. A pharmaceutical composition comprising the amorphous form of Compound 1 according to claim 1 and at least one pharmaceutically acceptable excipient.

19. An aqueous suspension comprising the amorphous form of Compound 1 according to claim 1 and at least one excipient.

20. An injectable or infusible solution comprising Compound 1 and at least one wetting agent or solvent, wherein the injectable or infusible solution is prepared using the amorphous form of Compound 1 according to claim 1.

21. A method for treating an individual suffering from or susceptible to a disease or disorder involving pathologic activation of C5a receptors, comprising administering to the individual an effective amount of an amorphous form of Compound 1 according to claim 1.

22. A pharmaceutical composition for oral use prepared using an amorphous form of Compound 1

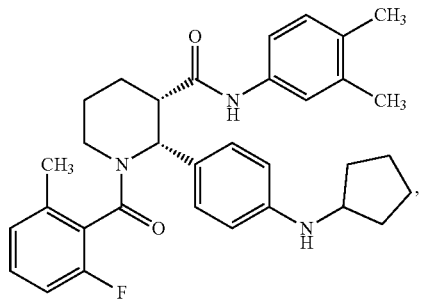

(Compound 1)

wherein the amorphous form of Compound 1 is characterized by an X-ray powder diffraction pattern having no distinct peaks, which is substantially free of other forms of Compound 1.

23. The pharmaceutical composition according to claim 22, wherein the amorphous form of Compound 1 is characterized by an X-ray powder diffraction pattern substantially in accordance with FIG. 2.

24. The pharmaceutical composition according to claim 22, wherein the amorphous form of Compound 1 is further characterized by a glass transition temperature of about 108° C., as determined by differential scanning calorimetry.

25. The pharmaceutical composition according to claim 22, wherein the amorphous form of Compound 1 is further characterized by a differential scanning calorimetry (DSC) thermogram substantially in accordance with FIG. 4.

26. The pharmaceutical composition according to claim 22, wherein the amorphous form of Compound 1 is further characterized by a weight loss of about 0.015% up heating to around 235° C., as measured by thermal gravimetric analysis (TGA).

27. The pharmaceutical composition according to claim 22, wherein the amorphous form of Compound 1 is further characterized a thermal gravimetric analysis (TGA) thermogram substantially in accordance with FIG. 5.

28. The pharmaceutical composition according to claim 22, wherein the amorphous form of Compound 1 is further characterized by a weight gain of about 0.44% after undergoing a dynamic vapor sorption (DVS) cycle from about 0% relative humidity (RH) to about 95% RH at 25° C.

29. The pharmaceutical composition according to claim 22, wherein the amorphous form of Compound 1 is further characterized by a weight gain of about 0.31% after undergoing a dynamic vapor sorption (DVS) cycle from about 0% relative humidity (RH) to about 65% RH at 25° C.

30. The pharmaceutical composition according to claim 22, wherein the amorphous form of Compound 1 is further characterized by a dynamic vapor sorption (DVS) plot that does not exhibit any hysteresis between adsorption and desorption.

31. The pharmaceutical composition according to claim 22, wherein the amorphous form of Compound 1 is further characterized by a dynamic vapor sorption (DVS) plot substantially in accordance with FIG. 6.

32. The pharmaceutical composition according to claim 22, wherein the amorphous form of Compound 1 is further characterized by a scanning electron microscopy (SEM) image having predominantly spherical particles.

33. The pharmaceutical composition according to claim 22, wherein the amorphous form of Compound 1 comprises spherical particle sizes are about 2 μm to 50 μm, as determined by SEM.

34. The pharmaceutical composition according to claim 22, wherein the amorphous form of Compound 1 is further characterized by scanning electron microscopy (SEM) image substantially in accordance with FIG. 8A, FIG. 8B, FIG. 8C, or FIG. 8D.

35. The pharmaceutical composition according to claim 22, wherein the amorphous form of Compound 1 is further characterized by a polarized light microscope (PLM) profile lacking birefringence.

36. The pharmaceutical composition according to claim 22, wherein the amorphous form of Compound 1 is further characterized by a polarized light microscope (PLM) profile substantially as shown in FIG. 9A, FIG. 9B, or FIG. 9C.

37. A method for treating an individual suffering from or susceptible to a disease or disorder involving pathologic activation of C5a receptors, comprising administering to the individual an effective amount of a pharmaceutical composition according to claim 22.

38. The method of claim 37, wherein the disease or disorder is selected from the group consisting of rheumatoid arthritis, C3 glomerulopathy (C3G), hidradenitis suppurativa (HS), systemic lupus erythematosus, Guillain-Barre syndrome, pancreatitis, lupus nephritis, lupus glomerulonephritis, psoriasis, immunoglobulin A (IgA) nephropathy, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome, immunovasculitis, tissue graft rejection and hyperacute rejection of transplanted organs.

39. The method of claim 37, wherein the disease or disorder is anti-neutrophil cytoplasmic antibody associate (ANCA) vasculitis.

40. The method of claim 39, wherein the disease or disorder is granulomatosis with polyangiitis.

41. The method of claim 39, wherein the disease or disorder is microscopic polyangiitis.

42. The method of claim 37, wherein the disease or disorder is C3 glomerulopathy.

43. The method of claim 37, wherein the disease or disorder is hidradenitis suppurativa.

\* \* \* \* \*

UNITED STATES PATENT AND TRADEMARK OFFICE
CERTIFICATE OF CORRECTION

PATENT NO. : 11,603,356 B2
APPLICATION NO. : 17/091001
DATED : March 14, 2023
INVENTOR(S) : Kwok Yau et al.

It is certified that error appears in the above-identified patent and that said Letters Patent is hereby corrected as shown below:

In the Claims

Column 24, Line 20, replace Compound 1 as shown:

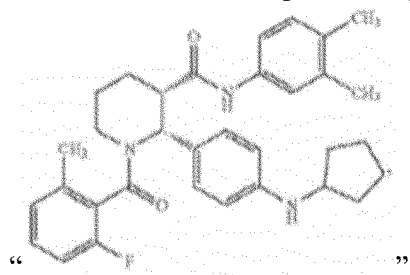

With:

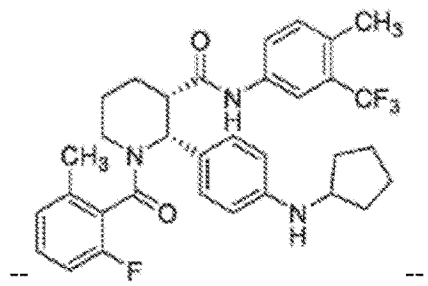

Signed and Sealed this
Fifth Day of August, 2025

Coke Morgan Stewart
*Acting Director of the United States Patent and Trademark Office*